US008858950B2

(12) United States Patent
Pardridge et al.

(10) Patent No.: US 8,858,950 B2
(45) Date of Patent: Oct. 14, 2014

(54) DELIVERY OF PHARMACEUTICAL AGENTS VIA THE HUMAN INSULIN RECEPTOR

(75) Inventors: William M. Pardridge, Pacific Palisades, CA (US); Ruben J. Boado, Agoura Hills, CA (US)

(73) Assignee: The Regents of the University of California, Oakland, CA (US)

( * ) Notice: Subject to any disclaimer, the term of this patent is extended or adjusted under 35 U.S.C. 154(b) by 336 days.

(21) Appl. No.: 12/150,983

(22) Filed: May 1, 2008

(65) Prior Publication Data

US 2009/0068206 A1 Mar. 12, 2009

Related U.S. Application Data

(62) Division of application No. 10/307,276, filed on Nov. 27, 2002, now Pat. No. 7,388,079.

(51) Int. Cl.
*A61K 39/40* (2006.01)
*A61K 39/395* (2006.01)
*C07K 16/28* (2006.01)
*A61K 47/48* (2006.01)
*C07K 16/00* (2006.01)
*A61K 39/00* (2006.01)

(52) U.S. Cl.
CPC ....... *C07K 16/2869* (2013.01); *A61K 2039/505* (2013.01); *A61K 47/48561* (2013.01); *C07K 2317/24* (2013.01)
USPC .................. 424/178.1; 424/130.1; 424/133.1; 424/134.1; 424/141.1; 424/143.1

(58) Field of Classification Search
None
See application file for complete search history.

(56) References Cited

U.S. PATENT DOCUMENTS

| | | | |
|---|---|---|---|
| 4,801,575 A | 1/1989 | Pardridge | |
| 4,902,505 A | 2/1990 | Pardridge et al. | |
| 5,154,924 A | 10/1992 | Friden | |
| 5,180,820 A | 1/1993 | Barde et al. | |
| 5,229,500 A | 7/1993 | Barde et al. | |
| 5,438,121 A | 8/1995 | Barde et al. | |
| 5,453,361 A | 9/1995 | Yancopoulos et al. | |
| 5,527,288 A | 6/1996 | Gross et al. | |
| 5,585,089 A | 12/1996 | Queen et al. | |
| 5,618,920 A | 4/1997 | Robinson et al. | |
| 5,656,284 A | 8/1997 | Balkin | |
| 5,672,683 A | 9/1997 | Friden et al. | |
| 5,693,761 A | 12/1997 | Queen et al. | |
| 5,693,762 A | 12/1997 | Queen et al. | |
| 5,824,782 A | 10/1998 | Holzer et al. | |
| 5,837,231 A | 11/1998 | Low et al. | |
| 5,848,991 A | 12/1998 | Gross et al. | |
| 5,929,304 A | 7/1999 | Radin et al. | |
| 5,977,307 A | 11/1999 | Friden et al. | |
| 5,997,501 A | 12/1999 | Gross et al. | |
| 6,041,775 A | 3/2000 | Century | |
| 6,060,069 A | 5/2000 | Hill et al. | |
| 6,153,190 A | 11/2000 | Young et al. | |
| 6,165,783 A | 12/2000 | Weiss et al. | |
| 6,284,262 B1 | 9/2001 | Place | |
| 6,287,792 B1 | 9/2001 | Pardridge et al. | |
| 6,322,808 B1 | 11/2001 | Trautman et al. | |
| 6,329,508 B1 | 12/2001 | Friden | |
| 6,348,210 B1 | 2/2002 | Gale | |
| 6,361,760 B1 | 3/2002 | Murata et al. | |
| 6,372,250 B1 | 4/2002 | Pardridge et al. | |
| 6,375,975 B1 | 4/2002 | Modi | |
| 6,583,272 B1 | 6/2003 | Bailon | |
| 6,743,427 B1 | 6/2004 | Schenk | |
| 7,053,202 B2 | 5/2006 | O'keefe et al. | |
| 7,078,376 B1 | 7/2006 | Thompson | |
| 7,226,758 B1 | 6/2007 | Lin et al. | |
| 7,294,704 B2 | 11/2007 | Simon et al. | |
| 7,309,687 B1 | 12/2007 | Brines et al. | |
| 7,388,079 B2 | 6/2008 | Pardridge et al. | |
| 2002/0025313 A1 | 2/2002 | Micklus et al. | |
| 2002/0137684 A1 | 9/2002 | Tchistiakova et al. | |
| 2002/0169109 A1 | 11/2002 | Plata-Salaman et al. | |
| 2003/0039649 A1 | 2/2003 | Foote | |
| 2003/0129186 A1 | 7/2003 | Beliveau et al. | |
| 2003/0165853 A1 | 9/2003 | Pardridge et al. | |
| 2004/0072291 A1 | 4/2004 | Carr et al. | |
| 2004/0101904 A1 | 5/2004 | Pardridge et al. | |
| 2004/0102369 A1 | 5/2004 | Wu et al. | |

(Continued)

FOREIGN PATENT DOCUMENTS

| | | |
|---|---|---|
| WO | WO 92/11018 A1 | 7/1992 |
| WO | WO 98/23761 A1 | 6/1998 |
| WO | WO 99/00150 A2 | 1/1999 |
| WO | WO 00/15759 A1 | 3/2000 |

OTHER PUBLICATIONS

Bost et al. Immunol. Invest. 1988; 17:577-586.*
Bendayan J. Histochem. Cytochem. 1995; 43:881-886.*

(Continued)

*Primary Examiner* — Chun Dahle
(74) *Attorney, Agent, or Firm* — Quine Intellectual Property Law Group, P.C.

(57) ABSTRACT

A humanized murine antibody is provided that binds to the human insulin receptor (HIR). The humanized murine antibody is suitable for use as a Trojan horse to deliver pharmaceutical agents to human organs and tissue that express the HIR. The humanized murine antibody is especially well suited for delivering neuropharmaceutical agents from the blood stream to the brain across the blood brain barrier (BBB). The humanized murine antibody may be genetically fused to the pharmaceutical agent or it may be linked to the pharmaceutical agent using an avidin-biotin conjugation system.

8 Claims, 5 Drawing Sheets

(56) References Cited

U.S. PATENT DOCUMENTS

| | | |
|---|---|---|
| 2005/0142141 A1 | 6/2005 | Pardridge et al. |
| 2007/0081992 A1 | 4/2007 | Pardridge et al. |
| 2007/0082380 A1 | 4/2007 | Pardridge et al. |
| 2007/0275882 A1 | 11/2007 | Meijer et al. |
| 2008/0051564 A1 | 2/2008 | Pardridge et al. |
| 2009/0068206 A1 | 3/2009 | Pardridge et al. |
| 2009/0156498 A1 | 6/2009 | Pardridge et al. |
| 2009/0238789 A1 | 9/2009 | Guyon et al. |
| 2010/0172919 A1 | 7/2010 | Grimm et al. |
| 2010/0261647 A1 | 10/2010 | Pardridge et al. |
| 2011/0112018 A1 | 5/2011 | Ehrenreich et al. |

OTHER PUBLICATIONS

Rudikoff et al. PNAS 1982 vol. 79 pp. 1979-1983.*
Amit et al. Science vol. 233, pp. 747-753, 1986.*
MacCallum et al. J. Mol. Biol. (1996) 262, 732-745.*
Pascalis et al. The Journal of Immunology (2002) 169, 3076-3084.*
Casset et al. BBRC(2003) 307, 198-205.*
Vajdos et al. JMB (2002) 320, 415-428.*
Holm et al. Molecular Immunology (2007) 44, 1075-1084.*
Colman et al. Research in Immunology, 1994; 145(1): 33-36.*
Amit et al. (1986) "Three-dimensional structure of an antigen-antibody complex at 2.8 A resolution." *Science*, 233(4756): 747-753.
Brummell et al. (1993) "Probing the Combining Site of an Anti-Carbohydrate Antibody by Saturation-Mutagenesis: Role of the Heavy-Chain CDR3 Residues." *Biochemistry*, 32: 1180-1187.
Coloma et al. (2000) "Transport Across the Primate Blood-Brain Barrier of a Genetically Engineered Chimeric Monoclonal Antibody to the Human Insulin Receptor." *Pharmaceutical Research*, 17(3): 266-274.
Daugherty et al. (1998) "Antibody affinity maturation using bacterial surface display." *Protein Engineering*, 11(9): 825-832.
Hwang et al. (2005) "Immunogenicity of engineered antibodies." *Methods*, 36: 3-10.
Moos and Morgan (2001) "Restricted transport of anti-transferrin receptor antibody (OX26) through the blood-brain barrier in the rat." *Journal of Neurochemistry*, 79: 119-129.
Padlan et al. (1995) "Identification of Specificity Determining Residues in Antibodies." *The FASEB Journal*, 9: 133-139.
Pardridge et al. (1995) "Human Insulin Receptor Monoclonal Antibody Undergoes High Affinity Binding to Human Brain Capillaries in Vitro and Rapid Trancytosis Through the Blood-Brain Barrier in Vivo in the Primate." *Pharmaceutical Research*, 12(6): 807-816.
Penichet et al. (1999) "An Antibody-Avidin Fusion Protein Specific for the Transferrin Receptor Serves as a Delivery Vehicle for Effective Brain Targeting: Initial Applications in Anti-HIV Antisense Drug Delivery to the Brain." *Journal of Immunology*, 163: 4421-4426.
Reichert (2001) Monoclonal antibodies in the clinic. *Nature Biotechnology*, 19: 819-822.
Rosenstein et al. (2001) "The Prevalence of Insulin Receptor Antibodies in Patients with Systemic Lupus Erythematosus and Related Conditions." *Journal of Clinical Rheumatology*, 7: 371-373.
Rudikoff et al. (1982) "Single Amino Acid Substitution Altering Antigen-Binding Specificity." *Proceedings of the National Academy of Sciences*, USA, 79(6): 1979-1983.
Salvetti et al. (2002) "Insulin permeability across an in vitro dynamic model of endothelium." *Pharmaceutical Research*, 19(4): 445-450.
Thompson et al. (1996) "Affinity Maturation of a High-affinity Human Monoclonal Antibody Against the Third Hypervariable Loop of Human Immunodeficiency Virus: Use of Phage Display to Improve Affinity and Broaden Strain Reactivity." *Journal of Molecular Biology*, 256: 77-88.
Vitetta and Ghetie (2006) "Considering Therapeutic Antibodies." *Science*, 313: 308-309.
Wu et al. (1998) "Stepwise in vitro affinity maturation of Vitaxin, an $\alpha v \beta_3$-specific humanized mAb." *Proceedings of the National Academy of Sciences*, USA, 95: 6037-6042.
Yelton et al. (1995) "Affinity maturation of the BR96 anti-carcinoma antibody by codon-based mutagenesis." *Journal of Immunology*, 155: 1994-2004.
Foote and Winter (1992) "Antibody Framework Residues Affecting the Conformation of the Hyperveriable Loops." *Journal of Molecular Biology*, 224: 487-499.
Li et al. (1999) "Genetically engineered brain drug delivery vectors: cloning, expression and in vivo application of an anti-transferrin receptor single chain antibody—streptavidin fusion gene and protein." *Protein Engineering*, 12(9): 787-796.
McCafferty and Glover (2000) "Engineering therapeutic proteins." *Current Opinion on Structural Biology*, 10: 417-420.
Pardridge (2001) "Brain Drug Targeting and Gene Technologies." *Japanese Journal of Pharmacology*, 87: 97-103.
Wu et al. (1997) "Drug Targeting of a Peptide Radiopharmaceutical through the Primate Blood-Brain Barrier in Vivo with a Monoclonal Antibody to the Human Insulin Receptor." *The Journal of Clinical Investigation*, 100(7): 1804-1812.
Insulin Receptor alpha antibody [83-14] Abcam catalog pages. 06/330/2010. pp. 1-2.
McGrath et al. (1997) "Bifuncational Fusion Between Nerve Growth Factor and a Transferrin Receptor Antibody." *Journal of Neuroscience Research*, 47: 123-133.
Wu et al. (1999) "Humanization of a Murine Monoclonal Antibody by Simultaneous Optimization of Framework and CDR Residues." *Journal of Molecular Biology*, 294: 151-162.
Boado & Pardridge (2010) "Genetic engineering of IgG-glucuronidase fusion proteins," Journal of Drug Targeting, 18(3):205-211.
Melton & Sherwood (1996) "Antibody-enzyme conjugates for cancer therapy," Journal of the National Cancer Institute, 88(3/4):153-165.
Vargas-Madrazo et al. (1997) "Evolution of the structural repertoire of the human $V_H$ and $V_K$ germline genes," International Immunology, 9(12): 1801-1815.
83-14 antibody PubMed results, Jun. 30, 2010, pp. 1-2.
Abcam catalog, Insulin Receptor alpha antibody, Certificate of Compliance, Oct. 3, 2011, p. 1.
Bachis, et al. 2003. Brain-Derived Neurotropic Factor Inhibits Human Immunodeficiency Virus-I/gp 120—Mediated Cerebellar Granule Cell Death by Preventing gp120 Internalization. *The Journal of Neuroscience* 23(13):5715-5722.
Baloh, et al. Functional mapping of receptor specificity domains of glial cell line derived neurotrophic factor (GDNF) family ligands and production of GFRalphal RETspecific agonists. *J Biol Chem.* Feb. 4, 2000; 275(5):3412-20.
Beck, et al. 1994. Brain-Derived Neurotropic Factor Protects Against Ischemic Cell Damage in Rat Hippocampus. *Journal of Cerebral Blood Flow and Metabolism* 14:689-692.
Bifrare, et al. 2005. Brain-Derived Neurotropic Factor Protects against Multiple Forms of Brain Injury in Bacterial Meningitis. *The Journal of Infectious Diseases.* 191:40-45.
Brines, et al. Erythropoietin crosses the blood-brain barrier to protect against experimental brain injury, *Proc Natl Acad Sci USA.* 2000; 97:10526-10531.
Burgess, et al. Possible dissociation of the heparin-binding and mitogenic activities of heparin-binding (acidic fibroblast) growth factor-1 from its receptor-binding activities by site-directed mutagenesis of a single lysine residue. *J Cell Biol.* Nov. 1990; 111(5 Pt 1):2129-38.
Carnicella, et al. GDNF is a fast-acting potent inhibitor of alcohol consumption and relapse. *Proc Natl Acad Sci USA.* Jun. 10, 2008; 105(23):8114-9.
Chen, et al. In vitro scanning saturation mutagenesis of all the specificity determining residues in an antibody binding site. *Protein Engineering.* 1999; 12(4):349-356.
Cheng, et al. 2004. Neuroprotection for Ischemic Stroke: Two Decades of Success and Failure. *The Journal of the American Society for Experimental NeuroTherapeutics.* 1:36-45.
Ehrenreich, et al. Erythropoietin therapy for acute stroke is both safe and beneficial. *Mol Med.* Aug. 2002; 8(8):495-505.

(56) References Cited

OTHER PUBLICATIONS

Eketjall, et al. Distinct structural elements in GDNF mediate binding to GFRalpha1 and activation of the GFRalpha1-c-Ret receptor complex. *EMBO J.* Nov. 1, 1999; 18(21):5901-10.

Eslamboli et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. *J. Neurosci.* 2005; 25:769-777.

Ferber, D. Bridging the blood-brain barrier: new methods improve the odds of getting drugs to the brain cells that need them. *PLoS Biol.* Jun. 2007; 5(6):e169: 1191-1194.

Fillebeen, et al. Receptor-mediated transcytosis of lactoferrin through the bloodbrain barrier. *J Biol Chem.* Mar. 12, 1999; 274(11):7011-7017.

Forough, et al. Differential transforming abilities of non-secreted and secreted forms of human fibroblast growth factor-1. *J Biol Chem.* Feb. 5, 1993; 268(4):2960-8.

Haisma, et al. Construction and characterization of a fusion protein of single-chain anti-CD2O antibody and human beta-glucuronidase for antibody-directed enzyme prodrug therapy. *Blood.* Jul. 1, 1998; 92(1):184-90.

He, et al. Autoregulation of glial cell line-derived neurotrophic factor expression: implications for the long-lasting actions of the anti-addiction drug, Ibogaine. FASEB J. Nov. 2006; 20(13):E1820-E1827; 2420-2422.

He, et al. Glial cell line-derived neurotrophic factor mediates the desirable actions of the anti-addiction drug ibogaine against alcohol consumption. *J Neurosci.* Jan. 19, 2005;25(3):619-28.

Hetman, et al. 1999. Neuroprotection by Brain-derived Neurotropic Factor Is Mediated by Extracellular Signal-regulated Kinase and Phoshatidylinositol3-Kinase. *The Journal of Biological Chemistry* 274(32): 22569-22580.

Jefferies, et al. Analysis of lymphopoietic stem cells with a monoclonal antibody to the rat transferrin receptor. *Immunology.* Feb. 1985; 54(2):333-41.

Jethwa, et al. 2005. Neuromedin U has a physiological role in the regulation of food intake and partially mediates the effects of leptin. *American Journal of Physiology-Endocrinology and Metabolism* 289:E301-E305.

Jiang, et al. 2005. BDNF Variation and Mood Disorders: A Novel Functional Promoter Polymorphism and Val66Met are Associated with Anxiety but Have Opposing Effects. *Neuropsychopharmacology* 30:1353-1361.

Kim, et al. 2004. Continuous Brain-derived Neurotropic Factor (BDNF) Infusion After Methylprednisolone Treatment in Severe Spinal Cord Injury. *Journal of Korean Medical Science.* 19:113-122.

Kitagawa et al. Reduction of Ischemic Brain Injury by Topical Application of Glial Cell Line-Derived Neurotrophic Factor After Permanent Middle Cerebral Artery Occlusion in Rats. *Stroke.* 1998; 29:1417-1422.

Kobayashi, et al. Intracerebral Infusion of Glial Cell Line-Derived Neurotrophic Factor Promotes Striatal Neurogenesis After Stroke in Adult Rats. *Stroke.* 2006; 37:2361-2367.

Kurihara, et al. 1999. Imaging Brain Tumors by Targeting Peptide Radiopharmaceuticals through the Blood-Brain Barrier. *Cancer Research.* 59: 6159-6163.

Lazar, et al. Transforming growth factor alpha: mutation of aspartic acid 47 and leucine 48 results in different biological activities. *Mol Cell Biol.* Mar. 1988; 8(3):1247-52.

Lee, et al. 2002. Imaging Brain Amyloid of Alzheimer Disease in Vivo in Transgenic Mice With an Aβ Peptide Radiopharmaceutical. *Journal of Cerebral Blood Flow and Metabolism.* 22:223-231.

Martell, et al. Efficacy of transferrin receptor-targeted immunotoxins in brain tumor cell lines and pediatric brain tumors. *Cancer Res.* Mar. 15, 1993; 53(6):1348-53.

Marvin, et al. Recombinant approaches to IgG-like bispecific antibodies. *Acta Pharmacol Sin.* Jun. 2005; 26(6):649-58.

Matis, et al. Erythropoietin in spinal cord injury. *Eur Spine J.* Mar. 2009; 18(3):314-23.

Messer, et al. Role for GDNF in biochemical and behavioral adaptations to drugs of abuse. *Neuron.* Apr. 2000; 26(1):247-57.

Ohtsuka et al. An alternative approach to deoxyoligonucleotides as hybridization probes by insertion of Deoxyinosine at Ambiguous Codon Positions. *J. Biol. Chem.* 1985; 260:2605-2608.

Pardridge, 2001. Brain drug targeting: The future of brain drug development. Cambridge University Press.

Pardridge, 2003. Blood-Brain Barrier Drug Targeting: The Future of Brain Drug Development. *Molecular Interventions.* 3:90-105.

Pardridge, 2005. The Blood-Brain Barrier and Neurotherapeutics. *NeuroRx: The Journal of the American Society for Experimental Neuro Therapeutics.* 2(1):1-2.

Pardridge, 2005. The Blood-Brain Barrier: Bottleneck in Brain Drug Development. *NeuroRx: The Journal of the American Society for Experimental Neuro Therapeutics.* 2:3-14.

Pencea, et al. 2001. Infusion of Brain-Derived Neurotrophic Factor into the Lateral Ventricle of the Adult Rat Leads to New Neurons in the Parenchyma of the Striatum, Septum, Thalamus, and Hypothalamus. *The Journal of Neuroscience.* 21(17):6706-6717.

Sakanaka, et al. In vivo evidence that erythropoietin protects neurons from ischemic damage. *Proc Natl Acad Sci USA.* Apr. 14, 1998; 95(8):4635-40.

Sariola, et al. Novel functions and signalling pathways for GDNF. *J Cell Sci.* Oct. 1, 2003; 116(Pt 19):3855-62.

Schabitz, et al. 1997. Intraventricular Brain-Derived Neurotrophic Factor Reduces Infarct Size AAer Focal Cerebral lschemia in Rats. *Journal of Cerebral Blood Flow and Metabolism.* 17:500-506.

Schwartz, et al. A superactive insulin: [B10-aspartic acid]insulin(human). *Proc Natl Acad Sci USA.* Sep. 1987; 84(18):6408-11.

Selmayr, et al. Induction of tumor immunity by autologous B lymphoma cells expressing a genetically engineered idiotype. *Gene Ther.* May 1999; 6(5):778-84.

Shanafelt, et al. Identification of critical amino acid residues in human and mouse granulocyte-macrophage colony-stimulating factor and their involvement in species specificity. *J Biol Chem.* Jul. 25, 1991; 266(21):13804-10.

Shin, et al. Transferrin-antibody fusion proteins are effective in brain targeting, *Proceedings of the National Academy of Sciences*, 1995. 92:2820-2824.

Siren, et al., Erythropoetin prevents neuronal apoptosis after cerebral ischemia and metabolic stress. *Proc Natl Acad Sci USA.* Mar. 27, 2001; 98(7):4044-9.

Skolnick, et al. From genes to protein structure and function: novel applications of computational approaches in the genomic era. *Trends Biotechnol.* Jan. 2000; 18(1): 34-9. Review.

Thoenen, et al. 2002. Neurotrophins: from enthusiastic expectations through sobering experiences to rational therapeutic approaches. *Nature Neuroscience.* Supplement 5:1046-1050.

Wang, et al. Identification of the key amino acids of glial cell line-derived neurotrophic factor family receptor alphal involved in its biological function. *J Biol. Chem.* Jan. 2, 2004; 279(1):109-16.

Whetstone, et al. Blood-spinal cord barrier after spinal cord injury: relation to revascularization and wound healing. *J Neurosci Res.* Oct. 15, 2003; 74(2):227-39.

Wu, et al. 1999. Neuroprotection with noninvasive neurotrophin delivery to the brain. *Proceedings of the National Academy of Sciences USA: Neurobiology.* 96:254-259.

Yan, et al. Enduring vulnerability to reinstatement of methamphetamine-seeking behavior in glial-cell-line-derived neurotrophic factor mutant mice. *FASEB J.* Jul. 2007; 21(9):1994-2004.

Yip, et al. Three-dimensional structural interactions of insulin and its receptor. *J Biol Chem.* Jul. 25, 2003; 278(30):27329-32.

Zhang, et al. 2001. Neuroprotection in Transient Focal Brain lschemia After Delayed Intravenous Administration of Brain-Derived Neurotrophic Factor Conjugated to a Blood-Brain Barrier Drug Targeting System. *Stroke.* 32:1378-1384.

Alberts et al., 1994. Molecular Biology of the Cell, 3rd Edition, pp. 1206-1207.

Boado et al. Fusion Antibody for Alzheimer's Disease with Bi-Directional Transport Across the Blood-Brain Barrier and Abeta Fibril Disaggregation. *Bioconjug Chem.* 2007; 18(2):447-455.

(56) References Cited

OTHER PUBLICATIONS

Weich, et al. Interleukin-3/erythropoietin fusion proteins: in vitro effects on hematopoietic cells. *Exp Hematol.* May 1993; 21(5):647-655.
Al, et al., 2003. Intraputamenal Infusion of GDNF in Aged Rhesus Monkeys: Distribution and Dopaminergic Effects. *The Journal of Comparative Neurology* 461(2):250-261.
Airavaara, et al. Effects of repeated morphine on locomotion, place preference and dopamine in heterozygous glial cell line-derived neurotrophic factor knockout mice. *Genes Brain Behav.* Apr. 2007; 6(3):287-98.
Albayrak, et al. 1997. Effect of transient focal ischemia on blood-brain barrier permeability in the rat: Correlation to Cell Injury. *Acta Neuropathol.* 94:158-163.
Barth et al. Boron neutron capture therapy of brain tumors: an emerging therapeutic modality. *Neurosurgery.* Mar. 1999; 44(3):433-50; discussion 433-450.
Boado et al, Genetic engineering, expression, and activity of a fusion protein of a human neurotrophin and a molecular Trojan horse for delivery across the human bloodbrain barrier. *Biotechnology and Bioengineering.* 2007; 97:1376-1386.
Boado et al. Genetic engineering of a lysosomal enzyme fusion protein for targeted delivery across the human blood-brain barrier. *Biotechnology and Bioengineering.* 2008; 99:475-484.
Boado, et al. Engineering and expression of a chimeric transferrin receptor monoclonal antibody for blood-brain barrier delivery in the mouse. *Biotechnology and Bioengineering.* Mar. 1, 2009; 102(4):1251-8.
Boado, et al. GDNF fusion protein for targeted-drug delivery across the human blood-brain barrier. *Biotechnology and Bioengineering.* Jun. 1, 2008; 100(2):387-96.
Buchli, et al. Inhibition of Nogo: a key strategy to increase regeneration, plasticity and functional recovery of the lesioned central nervous system. *Ann Med.* 2005; 37(8):556-67.
Cheng, et al. 1997. Marked Age-dependent Neuroprotection by Brain-derived Neurotropic Factor Against Neonatal Hypoxic-Ischemic Brain Injury. *Annals of Neurology.* 41(4):521-529.
Coloma, et al. Design and production of novel tetravalent bispecific antibodies. *Nat. Biotechnol.* Feb. 1997; 15(2):159-63.
Coloma, et al. The hinge as a spacer contributes to covalent assembly and is required for function of IgG. *J Immunol.* Jan. 15, 1997; 158(2):733-40.
Cowen, et al. 2004. Neuropeptides: implications for alcoholism. *Journal of Neurochemistry.* 89:273-285.
Dawson, et al. 2001. A comparative assessment of the efficacy and side-effect liability of the neuroprotective compounds in experimental stroke. *Brain Research.* 892:344-350.
Deguchi, et al. Retention of biologic activity of human epidermal growth factor following conjugation to a blood-brain barrier drug delivery vector via an extended poly(ethylene glycol) linker. *Bioconjug Chem.* Jan.-Feb. 1999;10(1):32-7.
Dreier, et al. Recombinant immunocytokines targeting the mouse transferrin receptor: construction and biological activities. *Bioconjug Chem.* Jul.-Aug. 1998;9(4):482-9.
Duchnowska, et al. Central nervous system metastases in breast cancer patients administered trastummab *Cancer Treat Rev.* Jun. 2005; 31(4):312-8.
Duffy, et al. 1987. Blood-brain barrier transcytosis of insulin in developing rabbits. *Brain Research.* 420:32-38.
Elliott, et al. Control of rHuEPO biological activity: the role of carbohydrate. *Exp Hematol.* Dec. 2004; 32(12):1146-55.
Friden, et al. Blood-brain barrier penetration and in vivo activity of an NGF conjugate. *Science.* Jan. 15, 1993; 259(5093):373-377.
Fu, et al. Neuroprotection in stroke in the mouse with intravenous erythropoietin-Trojan horse fusion protein. *Brain Res.* Jan. 19, 2011; 1369:203-7. Epub Oct. 31, 2010.
Gillies, et al. Bi-functional cytokine fusion proteins for gene therapy and antibody targeted treatment of cancer. 2002, *Cancer Immunology and Immunotherapy*, vol. 51:449-460.

Grasso, et al. Neuroprotection by erythropoietin administration after experimental traumatic brain injury. *Brain Res.* Nov. 28, 2007; 1182:99-105.
Green-Sadan, et al. Transplantation of glial cell line-derived neurotrophic factor expressing cells into the striatum and nucleus accumbens attenuates acquisition of cocaine self-administration in rats. *Eur J Neurosci.* Oct. 2003; 18(7):2093-8.
Habgood, et al. Changes in blood-brain barrier permeability to large and small molecules following traumatic brain injury in mice. *Eur J Neurosci.* Jan. 2007; 25(1):231-8.
Hoshaw, et al. 2005. Central administration of IGF-I and BDNF leads to long-lasting antidepressant-like effects. *Brain Research.* 1037:204-208.
Ibanez, et al. An extended surface of binding to Trk tyrosine kinase receptors in NGF and BDNF allows the engineering of a multifunctional pan-neurotrophin. *EMBO J.* Jun. 1993; 12(6):2281-93.
Ibanez, Structure-function relationships in the neurotrophin family. *J Neurobiol.* Nov. 1994; 25(11):1349-61.
Iwasaki, et al. Protective effect of interleukin-3 and erythropoietin on motor neuron death after neonatal axotomy. *Neurol Res.* Oct. 2002; 24(7):643-6.
Juul, et al. Erythropoietin concentrations in cerebrospinal fluid of nonhuman primates and fetal sheep following high-dose recombinant erythropoietin, *Biol. Neonate.* 2004; 85:138-144.
Kastin et al. Glial cell line-derived neurotrophic factor does not enter normal mouse brain. *Neuroscience Letters.* 2003; 340:239-241.
Kido, et al. 2000. Neuroprotective effects of brain-derived neurotropic factor in eyes with NMDA-induced neuronal death. *Brain Research* 884:59-67.
Koehne, et al. Vascular endothelial growth factor and erythropoietin concentrations in cerebrospinal fluid of children with hydrocephalus. *Childs Nerv Syst.* Apr. 2002; 18(3-4):137-41.
Krewson, et al. 1995. Distribution of nerve growth factor following direct delivery to brain interstitium. *Brain Research.* 680:196-206.
Lai, et al. Structural determinants of Trk receptor specificities using BDNF-based neurotrophin chimeras. *J Neurosci Res.* Dec. 1, 1996; 46(5):618-29.
Lang et al. Randomized controlled trial of intraputamenal glial cell line-derived neurotrophic factor infusion in Parkinson disease. *Annals of Neurology.* 2006;59:459-466.
Lapchak et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. *Neuroscience.* 1997; 78:61-72.
Lin et al. GDNF: a glial cell line-derived neurotrophic factor for midbrain dopaminergic neurons. *Science.* 1993; 260:1130-1132.
Lin, et al. Structure-function relationships in glucagon: properties of highly purified des-His-1-, monoiodo-, and (des-Asn-28, Thr-29)(homoserine lactone-27)-glucagon. *Biochemistry.* Apr. 22, 1975; 14(8):1559-63.
Lu et al. Cationic Liposome-Mediated GDNF Gene Transfer after Spinal Cord Injury. *Journal of Neurotrauma.* 2002; 19:1081-1090.
Ma, et al. Erythropoietin protects PC12 cells from beta-amyloid(25-35)-induced apoptosis via PI3/Akt signaling pathway. *Neuropharmacology.* May-Jun. 2009;56(6-7):1027-34.
McLendon et al. Radiotoxicity of systemically administered 211At-labeled human/mouse chimeric monoclonal antibody: a long-term survival study with histologic analysis. *Int J Radiat Oncol Biol Phys.* Sep. 1, 1999; 45(2):491-9.
Menzies, et al. 1993. Contributions of ions and albumin to the formations and resolution of ischemic brain edema. *Journal of Neurosurgery.* 78:257-266.
Mori, et al. 2004. Differential expression patterns of TrkB ligands in the macaque monkey brain. Developmental Neuroscience 15: 2507-2511.
Nutt, et al. 2003. Randomized, double-blind trial of glial cell line-derived neurotropic factor (GDNF) in PD. *Neurology.* 60:69-73.
Pardridge, 2001. Neuroprotection in stroke: is it time to consider large-molecule drugs? *Drug Discovery Today.* 6:751-753.
Pardridge, 2002. Neurotrophins, neuroprotection and the blood-brain barrier. *Current Opinion in Investigational Drugs.* 3(12):1753-1757.

(56) References Cited

OTHER PUBLICATIONS

Pardridge, et al. 1987. Human Blood-Brain Barrier Transferrin Receptor. *Metabolism*. 36:892-895.
Pardridge, et al. 1994. Transport of Human Recombinant Brain-Derived Neurotrophic Factor (BDNF) Through the Rat Blood-Brain Barrier in Vivo Using Vector-Mediated Peptide Drug Delivery. *Pharmaceutical Research*. 11(5):738-746.
Pardridge, et al. 1998, Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. *Pharmaceutical Research*. 15 (4):576-582.
Pardridge, et al. Drug and gene targeting to the brain with molecular Trojan horses. *Nat Rev Drug Discov*. Feb. 2002; 1(2):131-9.
Pardridge. Drug Targeting to the Brain. *Pharmaceutical Research*. 2007; 23:1733-1744.
Park, et al. Production and characterization of fusion proteins containing transferrin and nerve growth factor. *J Drug Target*. 1998; 6(1):53-64.
Patel et al. Intraputamenal infusion of glial cell line-derived neurotrophic factor in PD: A two-year outcome study. *Annals of Neurology*. 2005; 57:298-302.
Pregi, et al. TNF-alpha-induced apoptosis is prevented by erythropoietin treatment on SH-SY5Y cells. *Exp Cell Res*. Feb. 1, 2009; 315(3):419-31. Epub Nov. 20, 2008.
Preston, et al. 1997. Evidence for pore-like opening of the blood-brain barrier following forebrain ischemia in rats. *Brain Research* 761:4-10.
Raghavan, et al. Analysis of the pH dependence of the neonatal Fc receptor/immunoglobulin G interaction using antibody and receptor variants. *Biochemistry*. Nov. 14, 1995; 34(45):14649-57.
Ratliff-Schaub, et al. 2005. Randomized controlled trial of transdermal secretion on behavior of children with autism. *Autism*. 9(3):256-265.
Reiber, et al. Protein transfer at the blood cerebrospinal fluid barrier and the quantitation of the humoral immune response within the central nervous system. *Clin Chim Acta*. Mar. 30, 1987; 163(3):319-28.
Robinson, et al. 1999. The structures of the neurotrophin 4 homodimer and the brain-derived neurotrophic factor I neurotrophin 4 heterodimer reveal a common Trk binding site. *Protein Science*. 8:2589-2597.
Ruiz-Leon, et al. 2003. Induction of Tyrosine Kinase Receptor B by Retinoic Acid Allows Brain-Derived Neurotrophic Factor-Induced Amyloid Precursor Protein Gene Expression in Human SHSYSY Neuroblastoma Cells. *Neuroscience*. 120:1019-1026.
Sakane, et al. 1997. Carboxyl-directed Pegylation of Brain-derived Neurotrophic Factor Markedly Reduces Systemic Clearance with Minimal Loss of Biologic Activity. *Pharmaceutical Research*. 14(8):1085-1091.
Schlachetzki, et al. Expression of the neonatal Fc receptor (FcRn) at the bloodbrain barrier. *J Neurochem*. Apr. 2002; 81(1):203-6.
Spina, et al. 1992. Brain-Derived Neurotrophic Factor Protects Dopamine Neurons Against 6-Hydroxydopamine and N-Methyl-4-Phenylpyridinium Ion Toxicity: Involvement of the Glutathione System. *Journal of Neurochemistry*. 59(1):99-106.
Takahashi, et al. 1991. Inhibition of cell growth and tumorigenesis of human glioblastoma cells by a neutralizing antibody against human basic fibroblast growth factor. *Federation of European Biochemical Societies*. 288 (1,2):65-71.
The BDNF Study Group (Phase 111). 1999. A controlled trial of recombinant methionyl human BDNF in ALS. *Neurology*. 52:1427-1433.
Triguero et al. Capillary depletion method for quantification of blood-brain barrier transport of circulating peptides and plasma proteins. *J Neurochem*. 1990; 54(6):1882-8.

Tsukahara, et al. 1994. The Role of Brain-derived Neurotrophic Factor in Transient Forebrain Ischemia in the Rat Brain. *Neurosurgery*. 34 (2):323-331.
Um, et al. A "classical" homodimeric erythropoietin receptor is essential for the antiapoptotic effects of erythropoietin on differentiated neuroblastoma SH-SY5Y and pheochromocytoma PC-12 cells. *Cell Signal*. Mar. 2007; 19(3):634-45.
Wiesenhofer et al. Glial cell line-derived neurotrophic factor (GDNF) and its receptor (GFR-al) are strongly expressed in human gliomas. *Acta Neuropathol*. (*Berl*). 2000; 99:131-137.
Xue, et al. Intrastriatal administration of erythropoietin protects dopaminergic neurons and improves neurobehavioral outcome in a rat model of Parkinson's disease. *Neuroscience*. May 25, 2007; 146(3):1245-58.
Yamashita, et al. 1997. Post-Occlusion Treatment with BDNF Reduces Infarct Size in a Model of Permanent Occlusion of the Middle Cerebral Artery in Rat. *Metabolic Brain Disease*. 12 (4):271-280.
Yan, et al. 1994. Distribution of Intracerebral Ventricularly Administered Neurotrophins in Rat Brain and Its Correlation with Trk Receptor Expression. *Experimental Neurology*. 127:23-36.
Zhang, et al. 2001. Conjugation of brain-derived neurotrophic factor to a blood-brain barrier drug targeting system enables neuroprotection in regional brain ischemia following intravenous injection of the neurotrophin. *Brain Research*. 889:49-56.
Zhang, et al. 2003. Global Non-Viral Gene Transfer to the Primate Brain Following Intravenous Administration. *Molecular Therapy*. 7(1):11-18.
Zhang, et al. Mediated efflux of IgG molecules from brain to blood across the blood-brain barrier. *J Neuroimmunol*. Mar. 1, 2001; 114(1-2):168-72.
Barth et al. Boron neutron capture therapy of brain tumors: an emerging therapeutic modality. *Neurosurgery*. Mar. 1999; 44(3):433-50; discussion 450-1.
Ma, et al. Erythropoietin protects PC12 cells from beta-amyloid(25-35)-induced apoptosis via PI3/Akt signaling pathway. *Neuropharmacology*. May-Jun. 2009; 56(6-7):1027-34.
Pardridge, et al. 1993. Transport of Human Recombinant Brain-Derived Neurotrophic Factor (BDNF) Through the Rat Blood-Brain Barrier in Vivo Using Vector-Mediated Peptide Drug Delivery. *Pharmaceutical Research*. 11(5):738-746.
Pardridge, et al. 1998, Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. *Pharmaceutical Research*. 15 (4):576-582.
Robinson, et al. 1999. The structures of the neurotrophin 4 homodimer and the brain-derived neurotrophic factor I neurotrophin 4 heterodimer reveal a common Trk binding site. Protein. *Science*. 8:2589-2597.
Tsukahara, et al. 1994. The Role of Brain-derived Neurotrophic Factor in Transient Forebrain lschemia in the Rat Brain. *Neurosurgery*. 34 (2):323-331.
Weich, et al. Interleukin-3/erythropoietin fusion proteins: in vitro effects on hematopoietic cells. *Exp Hematol*. May 1993; 21(5):647-55.
Boado et al. (2007) "Humanizationof Anti-Human Insulin Receptor Antibody for Drug Targeting Across the Human Blood-Brain Barrier." *Biotechnology and Bioengineering*, 96(2):381-391.
Bruggemann et al. (1989) "The Immunogenicity of Chimeric Antibodies." *Journal of Experimental Medicine*, 170: 2153-2157.
Pichla et al. (1997) "The Crystal Structure of a Fab Fragment to the Melanoma-Associated GD2 Ganglioside." *Journal of Structural Biology*, 119: 6-16.

\* cited by examiner

MURINE 83-14 VH NUCLEOTIDE AND AMINO ACID SEQUENCE

CAG GTC CAG CTG CAG GAG TCT GGA CCT GAG CTG GTG AAG CCT GGG GCT TTA GTG
gln val gln leu gln glu ser gly pro glu leu val lys pro gly ala leu val AAG ATA TCC TGC AAG GCT TCT GGT TAC ACC TTC ACA AAC TAC GAT ATA CAC TGG GTG AAG
lys ile ser cys lys ala ser <u>gly tyr thr phe thr asn tyr asp ile his</u> trp val lys
                                               VH-CDR1

CAG AGG CCT GGA CAG GGA CTT GAG TGG ATT GGA TGG ATT TAT CCT GGA GAT GGT AGT ACT
gln arg pro gly gln gly leu glu trp ile gly <u>trp ile tyr pro gly asp gly ser thr</u>
\*   \*   \*   \*   \*   \*   \*   \*   \*   \*   \*   \*   \*   \*   \*      VH-CDR2

AAG TAC AAT GAG AAA TTC AAG GGC AAG GCC ACA CTG ACT GCA GAC AAA TCC TCC AGC ACA
<u>lys tyr asn glu lys phe lys gly</u> lys ala thr leu thr ala asp lys ser ser ser thr
                                              \*   \*   \*   \*

GCC TAC ATG CAC CTC AGC AGC CTG ACT TCT GAG AAA TCT GCA GTC TAT TTC TGT GCA AGA
ala tyr met his leu ser ser leu thr ser glu lys ser ala val tyr phe cys ala arg
\*   \*   \*   \*   \*   \*   \*   \*   \*

GAG TGG GCT TAC TGG GGC CAA GGG ACT CTG GTC ACT GTC TCT GCA
<u>glu trp ala tyr</u> trp gly gln gly thr leu val thr val ser ala
\*   \*   \*   \*   \*   \*   \*   \*   \*   \*   \*   \*   \*   \*   \*
VH-CDR3

MURINE 83-14 VL NUCLEOTIDE AND AMINO ACID SEQUENCE

GAT ATC CAG ATG ACC CAA TCT CCA TCC TCC TTA TCT GCC TCT CTG GGA GAA AGA GTC AGT
asp ile gln met thr gln ser pro ser ser leu ser ala ser leu gly glu arg val ser
\*   \*   \*   \*   \*   \*   \*   \*   \*   \*   \*   \*   \*   \*   \*   \*

CTC ACT TGT CGG GCA AGT CAG GAC ATT GGT GGT AAC TTA TAC TGG CTT CAG CAG GGA CCA
leu thr cys <u>arg ala ser gln asp ile gly gly asn leu tyr</u> trp leu gln gln gly pro
                     VL-CDR1

GAT GGA ACT ATT AAA CGC CTG ATA TAC GCC ACA TCC AGT TTA GAT TCT GGT GTC CCC AAA
asp gly thr ile lys arg leu ile tyr <u>ala thr ser ser leu asp ser</u> gly val pro lys
                              VL-CDR2

AGG TTC AGT GGC AGT AGG TCT GGG TCA GAT TAT TCT CTC ACC ATC AGC AGC CTT GAG TCT
arg phe ser gly ser arg ser gly ser asp tyr ser leu thr ile ser ser leu glu ser GAA GAT TTT GTA GAC TAT TAC TGT CTA CAG TAT TCT AGT TCT CCG TGG ACG TTC GGT GGA
glu asp phe val asp tyr tyr cys <u>leu gln tyr ser ser ser pro trp thr</u> phe gly gly
                       VL-CDR3

GGC ACC AAG ATG GAA ATC AAA CGG
gly thr lys met glu ile lys arg

FIGURE 1

Heavy Chain

|  | FR1 | CDR1 | FR2 |
|---|---|---|---|
| humanized | QVQLLESGAELVRPGSSVKISCKAS | GYTFTNYDIH | WVKQRPGQGLEWIG |
| murine | QVQLQESGPELVKPGALVKISCKAS | GYTFTNYDIH | WVKQRPGQGLEWIG |
| human B43 | QVQLLESGAELVRPGSSVKISCKAS | GYAFSSYWMN | WVKQRPGQGLEWIG |
|  | 1 | 26 | 36 |

|  | CDR2 | FR3 |
|---|---|---|
| humanized | WIYPGDGSTKYNEKFKG | KATLTADKSSSTAYMHLSSLTSEKSAVYFCAR |
| murine | WIYPGDGSTKYNEKFKG | KATLTADKSSSTAYMHLSSLTSEKSAVYFCAR |
| human B43 | QIWPGDGDTNYNGKFKG | KATLTAD<u>E</u>SSSTAYM<u>Q</u>LSSL<u>R</u>SE<u>D</u>SAVY<u>S</u>CAR |
|  | 50 | 67 |

|  | CDR3 | FR4 |
|---|---|---|
| humanized | ----------EWAY | WGQGTTVTVSA |
| murine | ----------EWAY | WGQGTLVTVSA |
| human B43 | RETTTVGRYYYAMDY | WGQGTTVT--- |
|  | 99            99 | 103        113 |

Light Chain

|  | FR1 | CDR1 | FR2 |
|---|---|---|---|
| humanized | DIQMTQSPSSLSASVGDRVTITC | RASQDIGGNLY | WYQQKPGKAPKLLIY |
| murine | DIQMTQSPSSLSASLGERVSLTC | RASQDIGGNLY | WLQQGPDGTIKRLIY |
| REI | DIQMTQSPSSLSASVGDRVTITC | QASQDIIKYLN | WYQQKPGKAPKLLIY |
|  | 1 | 24 | 35 |

|  | CDR2 | FR3 |
|---|---|---|
| humanized | ATSSLDS | GVPSRFSGSGSGTDYTFTISSLQPEDIATYYC |
| murine | ATSSLDS | GVPKRFSGSRSGSDYSLTISSLESEDFVDYYC |
| REI | EASNLQA | GVPSRFSGSGSGTDYTFTISSLQPEDIATYYC |
|  | 50 | 57 |

|  | CDR3 | FR4 |
|---|---|---|
| humanized | LQYSSSPWT | FGQGTKVEIKR |
| murine | LQYSSSPWT | FGGGTKMEIKR |
| REI | QQYQSLPYT | FGQGTKVEIKR |
|  | 89 | 98        108 |

FIGURE 4

```
                             SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
           (A) LENGTH: 339 nucleotides
           (B) TYPE: nucleotide
           (C) STRANDEDNESS: single
           (D) TOPOLOGY: linear (ii) MOLECULE TYPE: nucleic acid (xi) SEQUENCE DESCRIPTION: SEQ ID NO: 1

CAGGTCCAGC TGCAGGAGTC TGGACCTGAG CTGGTGAAGC CTGGGGCTTT AGTGAAGATA        60

TCCTGCAAGG CTTCTGGTTA CACCTTCACA AACTACGATA TACACTGGGT GAAGCAGAGG       120

CCTGGACAGG GACTTGAGTG GATTGGATGG ATTTATCCTG GAGATGGTAG TACTAAGTAC       180

AATGAGAAAT TCAAGGGCAA GGCCACACTG ACTGCAGACA AATCCTCCAG CACAGCCTAC       240

ATGCACCTCA GCAGCCTGAC TTCTGAGAAA TCTGCAGTCT ATTTCTGTGC AAGAGAGTGG       300

GCTTACTGGG GCCAAGGGAC TCTGGTCACT GTCTCTGCA                             339

(2) INFORMATION FOR SEQ ID NO: 2:

(i) SEQUENCE CHARACTERISTICS:
           (A) LENGTH: 324 nucleotides
           (B) TYPE: nucleotide
           (C) STRANDEDNESS: single
           (D) TOPOLOGY: linear (ii) MOLECULE TYPE: nucleic acid (xi) SEQUENCE DESCRIPTION: SEQ ID NO: 2

GATATCCAGA TGACCCAATC TCCATCCTCC TTATCTGCCT CTCTGGGAGA AAGAGTCAGT        60

CTCACTTGTC GGGCAAGTCA GGACATTGGT GGTAACTTAT ACTGGCTTCA GCAGGGACCA       120

GATGGAACTA TTAAACGCCT GATATACGCC ACATCCAGTT TAGATTCTGG TGTCCCCAAA       180

AGGTTCAGTG GCAGTAGGTC TGGGTCAGAT TATTCTCTCA CCATCAGCAG CCTTGAGTCT       240

GAAGATTTTG TAGACTATTA CTGTCTACAG TATTCTAGTT CTCCGTGGAC GTTCGGTGGA       300

GGCACCAAGA TGGAAATCAA ACGG                                             324
```

(2) INFORMATION FOR SEQ ID NO: 3:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3 gln val gln leu gln glu ser gly pro glu leu val lys pro gly ala
1               5                   10                  15 leu val lys ile ser cys lys ala ser gly tyr thr phe thr asn tyr
            20                  25                  30 asp ile his trp val lys gln arg pro gly gln gly leu glu trp ile
        35                  40                  45 gly trp ile tyr pro gly asp gly ser thr lys tyr asn glu lys phe
    50                  55                  60 lys gly lys ala thr leu thr ala asp lys ser ser thr ala tyr
65                  70                  75                  80 met his leu ser ser leu thr ser glu lys ser ala val tyr phe cys
            85                  90                  95 ala arg glu trp ala tyr trp gly gln gly thr leu val thr val ser
            100                 105                 110 ala
113

(2) INFORMATION FOR SEQ ID NO: 4:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4 asp ile gln met thr gln ser pro ser ser leu ser ala ser leu gly
1               5                   10                  15 glu arg val ser leu thr cys arg ala ser gln asp ile gly gly asn
            20                  25                  30 leu tyr trp leu gln gln gly pro asp gly thr ile lys arg leu ile
        35                  40                  45 tyr ala thr ser ser leu asp ser gly val pro lys arg phe ser gly
    50                  55                  60 ser arg ser gly ser asp tyr ser leu thr ile ser ser leu glu ser
65                  70                  75                  80 glu asp phe val asp tyr tyr cys leu gln tyr ser ser ser pro trp
            85                  90                  95 thr phe gly gly gly thr lys met glu ile lys arg
            100                 105

(2) INFORMATION FOR SEQ ID NO: 5:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5 gln val gln leu leu glu ser gly ala glu leu val arg pro gly ser
1               5                   10                  15 ser val lys ile ser cys lys ala ser gly tyr thr phe thr asn tyr
                20                  25                  30 asp ile his trp val lys gln arg pro gly gln gly leu glu trp ile
                35                  40                  45 gly trp ile tyr pro gly asp gly ser thr lys tyr asn glu lys phe
            50                  55                  60 lys gly lys ala thr leu thr ala asp lys ser ser ser thr ala tyr
65                  70                  75                  80 met his leu ser ser leu thr ser glu lys ser ala val tyr phe cys
                85                  90                  95 ala arg glu trp ala tyr trp gly gln gly thr thr val thr val ser
                100                 105                 110 ala
113

(2) INFORMATION FOR SEQ ID NO: 6:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6 asp ile gln met thr gln ser pro ser ser leu ser ala ser val gly
1               5                   10                  15 glu arg val thr ile thr cys arg ala ser gln asp ile gly gly asn
                20                  25                  30 leu tyr trp tyr gln gln lys pro gly lys ala pro lys leu leu ile
                35                  40                  45 tyr ala thr ser ser leu asp ser gly val pro ser arg phe ser gly
            50                  55                  60 ser gly ser gly thr asp tyr thr phe thr ile ser ser leu gln pro
65                  70                  75                  80 glu asp ile ala thr tyr tyr cys leu gln tyr ser ser ser pro trp
                85                  90                  95 thr phe gly gln gly thr lys val glu ile lys arg
                100                 105

(2) INFORMATION FOR SEQ ID NO: 7:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7 gln val gln leu leu glu ser gly ala glu leu val arg pro gly ser
1               5                   10                  15

```
ser val lys ile ser cys lys ala ser gly tyr thr phe thr asn tyr
            20                  25                  30 asp ile his trp val lys gln arg pro gly gln gly leu glu trp ile
        35                  40                  45 gly trp ile tyr pro gly asp gly ser thr lys tyr asn glu lys phe
    50                  55                  60 lys gly gln ala thr leu thr ala asp lys ser ser ser thr ala tyr
65                  70                  75                  80 met gln leu ser ser leu thr ser glu asp ser ala val tyr ser cys
                85                  90                  95 ala arg glu trp ala tyr trp gly gln gly thr thr val thr val ser
                100                 105                 110 ala
113

(2) INFORMATION FOR SEQ ID NO: 8:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8 gln val gln leu leu glu ser gly ala glu leu val arg pro gly ser
1               5                   10                  15 ser val lys ile ser cys lys ala ser gly tyr thr phe thr asn tyr
            20                  25                  30 asp ile his trp val lys gln arg pro gly gln gly leu glu trp ile
        35                  40                  45 gly trp ile tyr pro gly asp gly ser thr lys tyr asn glu lys phe
    50                  55                  60 lys gly lys ala thr leu thr ala asp glu ser ser ser thr ala tyr
65                  70                  75                  80 met gln leu ser ser leu arg ser glu asp ser ala val tyr ser cys
                85                  90                  95 ala arg glu trp ala tyr trp gly gln gly thr thr val thr val ser
                100                 105                 110 ala
113

(2) INFORMATION FOR SEQ ID NO: 9:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9 gln val gln leu leu glu ser gly ala glu leu val arg pro gly ser
1               5                   10                  15 ser val lys ile ser cys lys ala ser gly tyr thr phe thr asn tyr
            20                  25                  30 asp ile his trp val lys gln arg pro gly gln gly leu glu trp ile
        35                  40                  45
```

```
gly trp ile tyr pro gly asp gly ser thr lys tyr asn glu lys phe
        50                  55                  60 lys gly lys ala thr leu thr ala asp glu ser ser thr ala tyr
 65                  70                  75                  80 met gln leu ser ser leu arg ser glu asp ser ala val tyr ser cys
                 85                  90                  95 ala arg glu trp ala tyr trp gly gln gly thr thr val thr val ser
             100                 105                 110 ala
113

(2) INFORMATION FOR SEQ ID NO: 10:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10 gln val gln leu gln glu ser gly pro glu leu val lys pro gly ala
 1                   5                  10                  15 leu val lys ile ser cys lys ala ser gly tyr thr phe thr asn tyr
                 20                  25                  30 asp ile his trp val lys gln arg pro gly gln gly leu glu trp ile
             35                  40                  45 gly trp ile tyr pro gly asp gly ser thr lys tyr asn glu lys phe
        50                  55                  60 lys gly lys ala thr leu thr ala asp glu ser ser thr ala tyr
 65                  70                  75                  80 met gln leu ser ser leu arg ser glu asp ser ala val tyr ser cys
                 85                  90                  95 ala arg glu trp ala tyr trp gly gln gly thr thr val thr val ser
             100                 105                 110 ala
113

(2) INFORMATION FOR SEQ ID NO: 11:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11 gln val gln leu leu glu ser gly ala glu leu val arg pro gly ser
 1                   5                  10                  15 ser val lys ile ser cys lys ala ser gly tyr thr phe thr asn tyr
                 20                  25                  30 asp ile his trp val lys gln arg pro gly gln gly leu glu trp ile
             35                  40                  45 gly trp ile tyr pro gly asp gly ser thr lys tyr asn glu lys phe
        50                  55                  60 lys gly lys ala thr leu thr ala asp lys ser ser ser thr ala tyr
```

```
              65                  70                  75                  80
met his leu ser ser leu thr ser glu lys ser ala val tyr phe cys
                        85                  90                  95 ala arg glu trp ala tyr trp gly gln gly thr leu val thr val ser
                100                 105                 110 ala
113

(2) INFORMATION FOR SEQ ID NO: 12:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12 gln val gln leu leu glu ser gly ala glu leu val arg pro gly ser
1               5                   10                  15 ser val lys ile ser cys lys ala ser gly tyr ala phe ser ser tyr
                20                  25                  30 trp met asn trp val lys gln arg pro gly gln gly leu glu trp ile
            35                  40                  45 gly gln ile trp pro gly asp gly asp thr asn tyr asn gly lys phe
        50                  55                  60 lys gly lys ala thr leu thr ala asp glu ser ser ser thr ala tyr
65                  70                  75                  80 met gln leu ser ser leu arg ser glu asp ser ala val tyr ser cys
                        85                  90                  95 ala arg arg glu thr thr thr val gly arg tyr tyr tyr ala met asp
                100                 105                 110 tyr trp gly gln gly thr thr val thr
            115                 120

(2) INFORMATION FOR SEQ ID NO: 13:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13 asp ile gln met thr gln ser pro ser ser leu ser ala ser val gly
1               5                   10                  15 asp arg val thr ile thr cys gln ala ser gln asp ile ile lys tyr
                20                  25                  30 leu asn trp leu gln gln lys pro gly lys ala pro lys leu leu ile
            35                  40                  45 tyr glu ala ser asn leu gln ala gly val pro ser arg phe ser gly
        50                  55                  60 ser gly ser gly thr asp tyr thr phe thr ile ser ser leu gln pro
65                  70                  75                  80 glu asp ile ala thr tyr tyr cys gln gln tyr gln ser leu pro tyr
                        85                  90                  95
```

```
thr phe gly gln gly thr lys val glu ile lys arg
        100                 105
```

(2) INFORMATION FOR SEQ ID NO: 14:

(i) SEQUENCE CHARACTERISTICS:
        (A) LENGTH: 91 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 14

```
TAGGATATCC ACCATGGAGA CCCCCGCCCA GCTGCTGTTC CTGTTGCTGC TTTGGCTTCC    60

AGATACTACC GGTGACATCC AGATGACCCA G                                   91
```

(2) INFORMATION FOR SEQ ID NO: 15:

(i) SEQUENCE CHARACTERISTICS:
        (A) LENGTH: 90 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 15

```
GTCCTGACTA GCCCGACAAG TAATGGTCAC TCTGTCACCC ACGCTGGCGC TCAGGCTGCT    60

TGGGCTCTGG GTCATCTGGA TGTCGCCGGT                                     90
```

(2) INFORMATION FOR SEQ ID NO: 16:

(i) SEQUENCE CHARACTERISTICS:
        (A) LENGTH: 90 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 16

```
ATTACTTGTC GGGCTAGTCA GGACATTGGA GGAAACTTAT ATTGGTACCA ACAAAAGCCA    60

GGTAAAGCTC CAAAGTTACT GATCTACGCC                                     90
```

(2) INFORMATION FOR SEQ ID NO: 17:

(i) SEQUENCE CHARACTERISTICS:
        (A) LENGTH: 90 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 17

```
GGTGTAGTCG GTACCGCTAC CACTACCACT GAATCTGCTT GGCACACCAG AATCTAAACT    60

AGATGTGGCG TAGATCAGTA ACTTTGGAGC                                     90
```

(2) INFORMATION FOR SEQ ID NO: 18:

(i) SEQUENCE CHARACTERISTICS:
        (A) LENGTH: 90 nucleotides
        (B) TYPE: nucleotide
        (C) STRANDEDNESS: single
        (D) TOPOLOGY: linear

```
        (ii) MOLECULE TYPE: nucleic acid (xi) SEQUENCE DESCRIPTION: SEQ ID NO: 18

AGTGGTAGCG GTACCGACTA CACCTTCACC ATCAGCAGCT TACAGCCAGA GGACATCGCC      60

ACCTACTATT GCCTACAGTA TTCTAGTTCT                                      90

(2) INFORMATION FOR SEQ ID NO: 19:

(i) SEQUENCE CHARACTERISTICS:
            (A) LENGTH: 80 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 19

CCCGTCGACT TCAGCCTTTT GATTTCCACC TTGGTCCCTT GTCCGAACGT CCATGGAGAA      60

CTAGAATACT GTAGGCAATA                                                 80

(2) INFORMATION FOR SEQ ID NO: 20:

(i) SEQUENCE CHARACTERISTICS:
            (A) LENGTH: 24 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 20

TAGGATATCC ACCATGGAGA CCCC                                            24

(2) INFORMATION FOR SEQ ID NO: 21:

(i) SEQUENCE CHARACTERISTICS:
            (A) LENGTH: 24 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 21

CCCGTCGACT TCAGCCTTTT GATT                                            24

(2) INFORMATION FOR SEQ ID NO: 22:

(i) SEQUENCE CHARACTERISTICS:
            (A) LENGTH: 94 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 22

TAGGATATCC ACCATGGACT GGACCTGGAG GGTGTTATGC CTGCTTGCAG TGGCCCCCGG      60

AGCCCACAGC CAAGTGCAGC TGCTCGAGTC TGGG                                 94

(2) INFORMATION FOR SEQ ID NO: 23:

(i) SEQUENCE CHARACTERISTICS:
            (A) LENGTH: 93 nucleotides
            (B) TYPE: nucleotide
```

(C) STRANDEDNESS: single
            (D) TOPOLOGY: linear (ii) MOLECULE TYPE: nucleic acid (xi) SEQUENCE DESCRIPTION: SEQ ID NO: 23

GTTTGTGAAG GTGTAACCAG AAGCCTTGCA GGAAATCTTC ACTGAGGACC CAGGCCTCAC        60

CAGCTCAGCC CCAGACTCGA GCAGCTGCAC TTG                                    93

(2) INFORMATION FOR SEQ ID NO: 24:

(i) SEQUENCE CHARACTERISTICS:
            (A) LENGTH: 93 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 24

GCTTCTGGTT ACACCTTCAC AAACTACGAT ATACACTGGG TGAAGCAGAG GCCTGGACAG        60

GGTCTTGAGT GGATTGGATG GATTTATCCT GGA                                    93

(2) INFORMATION FOR SEQ ID NO: 25:

(i) SEQUENCE CHARACTERISTICS:
            (A) LENGTH: 93 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 25

GCTGGAGGAT TCGTCTGCAG TCAGAGTGGC TTTGCCCTTG AATTTCTCAT TGTACTTAGT        60

ACTACCATCT CCAGGATAAA TCCATCCAAT CCA                                    93

(2) INFORMATION FOR SEQ ID NO: 26:

(i) SEQUENCE CHARACTERISTICS:
            (A) LENGTH: 93 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 26

CTGACTGCAG ACGAATCCTC CAGCACAGCC TACATGCAAC TAAGCAGCCT ACGATCTGAG        60

GACTCTGCGG TCTATTCTTG TGCAAGAGAG TGG                                    93

(2) INFORMATION FOR SEQ ID NO: 27:

(i) SEQUENCE CHARACTERISTICS:
            (A) LENGTH: 69 nucleotides
            (B) TYPE: nucleotide
            (C) STRANDEDNESS: single
            (D) TOPOLOGY: linear (ii) MOLECULE TYPE: nucleic acid (xi) SEQUENCE DESCRIPTION: SEQ ID NO: 27

CATGCTAGCA GAGACGGTGA CTGTGGTCCC TTGTCCCCAG TAAGCCCACT CTCTTGCACA        60

AGAATAGAC                                                               69

(2) INFORMATION FOR SEQ ID NO: 28:

(i) SEQUENCE CHARACTERISTICS:
        (A) LENGTH: 27 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 28

TAGGATATCC ACCATGGACT GGACCTG                                                    27

(2) INFORMATION FOR SEQ ID NO: 29:

(i) SEQUENCE CHARACTERISTICS:
        (A) LENGTH: 25 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 29

CATGCTAGCA GAGACGGTGA CTGTG                                                      25

(2) INFORMATION FOR SEQ ID NO: 30:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: nucleic acid (xi) SEQUENCE DESCRIPTION: SEQ ID NO: 30 gln val gln leu leu glu ser gly ala glu leu val arg pro gly ser
1               5                   10                  15 ser val lys ile ser cys lys ala ser
            20                  25

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 31 gly tyr thr phe thr asn tyr asp ile his
1               5                   10

(2) INFORMATION FOR SEQ ID NO: 32:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 32 trp val lys gln arg pro gly gln gly leu glu trp ile gly (2) INFORMATION FOR SEQ ID NO: 33:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 33

```
trp ile tyr pro gly asp gly ser thr lys tyr asn glu lys phe lys
1               5                   10                  15
gly
17
```

(2) INFORMATION FOR SEQ ID NO: 34:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 34

```
lys ala thr leu thr ala asp lys ser ser ser thr ala tyr met his
1               5                   10                  15
leu ser ser leu thr ser glu lys ser ala val tyr phe cys ala arg
            20                  25                  30
```

(2) INFORMATION FOR SEQ ID NO: 35:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 35

```
glu trp ala tyr
1           4
```

(2) INFORMATION FOR SEQ ID NO: 36:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 36

```
trp gly gln gly thr thr val thr val ser ala
1               5                   10
```

(2) INFORMATION FOR SEQ ID NO: 37:

(i) SEQUENCE CHARACTERISTICS:
        (A) LENGTH: 23 amino acids
        (B) TYPE: amino acid
        (C) STRANDEDNESS: single (D) TOPOLOGY: linear (ii) MOLECULE TYPE: polypeptide (xi) SEQUENCE DESCRIPTION: SEQ ID NO: 37 asp ile gln met thr gln ser pro ser ser leu ser ala ser leu gly
1               5                   10                  15 glu arg val thr ile thr cys
                20

(2) INFORMATION FOR SEQ ID NO: 38:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 38 arg ala ser gln asp ile gly gly asn leu tyr
1               5                   10

(2) INFORMATION FOR SEQ ID NO: 39:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 39 trp tyr gln gln lys pro gly lys ala pro lys leu leu ile tyr
1               5                   10                  15

(2) INFORMATION FOR SEQ ID NO: 40:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 40 ala thr ser ser leu asp ser
1               5

(2) INFORMATION FOR SEQ ID NO: 41:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 41 gly val pro ser arg phe ser gly ser gly ser gly thr asp tyr thr
1               5                   10                  15 phe thr ile ser ser leu gln pro glu asp ile ala thr tyr tyr cys
                20                  25                  30

(2) INFORMATION FOR SEQ ID NO: 42:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: polypeptide (xi) SEQUENCE DESCRIPTION: SEQ ID NO: 42 leu gln tyr ser ser ser pro trp thr
1               5

(2) INFORMATION FOR SEQ ID NO: 43:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: polypeptide (xi) SEQUENCE DESCRIPTION: SEQ ID NO: 43 phe gly gln gly thr lys val glu ile lys arg
1               5                   10

(2) INFORMATION FOR SEQ ID NO: 44:

(i) SEQUENCE CHARACTERISTICS:
       (A) LENGTH: 98 amino acids
       (B) TYPE: amino acid
       (C) STRANDEDNESS: single
       (D) TOPOLOGY: linear (ii) MOLECULE TYPE: polypeptide (xi) SEQUENCE DESCRIPTION: SEQ ID NO: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
    98

(2) INFORMATION FOR SEQ ID NO: 45:

(i) SEQUENCE CHARACTERISTICS:
       (A) LENGTH: 113 amino acids
       (B) TYPE: amino acid
       (C) STRANDEDNESS: single
       (D) TOPOLOGY: linear (ii) MOLECULE TYPE: polypeptide (xi) SEQUENCE DESCRIPTION: SEQ ID NO: 45

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys
113
```

(2) INFORMATION FOR SEQ ID NO: 46:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 46

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

(2) INFORMATION FOR SEQ ID NO: 47:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 47

```
Glu Pro Lys Ser Cys Asp Lys Thr His Thr Cys Pro
1               5                   10
```

(2) INFORMATION FOR SEQ ID NO: 48:

(i) SEQUENCE CHARACTERISTICS:
        (A) LENGTH: 626 amino acids (B) TYPE: amino acid
(C) STRANDEDNESS: single
(D) TOPOLOGY: linear (ii) MOLECULE TYPE: polypeptide (xi) SEQUENCE DESCRIPTION: SEQ ID NO: 48

```
Ala Pro His Leu Val Gln Val Asp Ala Ala Arg Ala Leu Trp Pro Leu
1               5                   10                  15

Arg Arg Phe Trp Arg Ser Thr Gly Phe Cys Pro Pro Leu Pro His Ser
            20                  25                  30

Gln Ala Asp Gln Tyr Val Leu Ser Trp Asp Gln Gln Leu Asn Leu Ala
        35                  40                  45

Tyr Val Gly Ala Val Pro His Arg Gly Ile Lys Gln Val Arg Thr His
50                  55                  60

Trp Leu Leu Glu Leu Val Thr Thr Arg Gly Ser Thr Gly Arg Gly Leu
65                  70                  75                  80

Ser Tyr Asn Phe Thr His Leu Asp Gly Tyr Leu Asp Leu Leu Arg Glu
            85                  90                  95

Asn Gln Leu Leu Pro Gly Phe Glu Leu Met Gly Ser Ala Ser Gly His
        100                 105                 110

Phe Thr Asp Phe Glu Asp Lys Gln Gln Val Phe Glu Trp Lys Asp Leu
            115                 120                 125

Val Ser Ser Leu Ala Arg Arg Tyr Ile Gly Arg Tyr Gly Leu Ala His
130                 135                 140

Val Ser Lys Trp Asn Phe Glu Thr Trp Asn Glu Pro Asp His His Asp
145                 150                 155                 160

Phe Asp Asn Val Ser Met Thr Met Gln Gly Phe Leu Asn Tyr Tyr Asp
                165                 170                 175

Ala Cys Ser Glu Gly Leu Arg Ala Ala Ser Pro Ala Leu Arg Leu Gly
            180                 185                 190

Gly Pro Gly Asp Ser Phe His Thr Pro Pro Arg Ser Pro Leu Ser Trp
            195                 200                 205

Gly Leu Leu Arg His Cys His Asp Gly Thr Asn Phe Phe Thr Gly Glu
210                 215                 220

Ala Gly Val Arg Leu Asp Tyr Ile Ser Leu His Arg Lys Gly Ala Arg
225                 230                 235                 240

Ser Ser Ile Ser Ile Leu Glu Gln Glu Lys Val Val Ala Gln Gln Ile
                245                 250                 255

Arg Gln Leu Phe Pro Lys Phe Ala Asp Thr Pro Ile Tyr Asn Asp Glu
            260                 265                 270

Ala Asp Pro Leu Val Gly Trp Ser Leu Pro Gln Pro Trp Arg Ala Asp
            275                 280                 285

Val Thr Tyr Ala Ala Met Val Lys Val Ile Ala Gln His Gln Asn
290                 295                 300

Leu Leu Leu Ala Asn Thr Thr Ser Ala Phe Pro Tyr Ala Leu Leu Ser
305                 310                 315                 320

Asn Asp Asn Ala Phe Leu Ser Tyr His Pro His Pro Phe Ala Gln Arg
                325                 330                 335

Thr Leu Thr Ala Arg Phe Gln Val Asn Asn Thr Arg Pro Pro His Val
            340                 345                 350

Gln Leu Leu Arg Lys Pro Val Leu Thr Ala Met Gly Leu Leu Ala Leu
            355                 360                 365

Leu Asp Glu Glu Gln Leu Trp Ala Glu Val Ser Gln Ala Gly Thr Val
370                 375                 380
```

```
Leu Asp Ser Asn His Thr Val Gly Val Leu Ala Ser Ala His Arg Pro
385                 390                 395                 400

Gln Gly Pro Ala Asp Ala Trp Arg Ala Ala Val Leu Ile Tyr Ala Ser
                405                 410                 415

Asp Asp Thr Arg Ala His Pro Asn Arg Ser Val Ala Val Thr Leu Arg
            420                 425                 430

Leu Arg Gly Val Pro Pro Gly Pro Gly Leu Val Tyr Val Thr Arg Tyr
        435                 440                 445

Leu Asp Asn Gly Leu Cys Ser Pro Asp Gly Glu Trp Arg Arg Leu Gly
    450                 455                 460

Arg Pro Val Phe Pro Thr Ala Glu Gln Phe Arg Arg Met Arg Ala Ala
465                 470                 475                 480

Glu Asp Pro Val Ala Ala Pro Arg Pro Leu Pro Ala Gly Gly Arg
                485                 490                 495

Leu Thr Leu Arg Pro Ala Leu Arg Leu Pro Ser Leu Leu Val His
                500                 505                 510

Val Cys Ala Arg Pro Glu Lys Pro Pro Gly Gln Val Thr Arg Leu Arg
    515                 520                 525

Ala Leu Pro Leu Thr Gln Gly Gln Leu Val Leu Val Trp Ser Asp Glu
    530                 535                 540

His Val Gly Ser Lys Cys Leu Trp Thr Tyr Glu Ile Gln Phe Ser Gln
545                 550                 555                 560

Asp Gly Lys Ala Tyr Thr Pro Val Ser Arg Lys Pro Ser Thr Phe Asn
                565                 570                 575

Leu Phe Val Phe Ser Pro Asp Thr Gly Ala Val Ser Gly Ser Tyr Arg
            580                 585                 590

Val Arg Ala Leu Asp Tyr Trp Ala Arg Pro Gly Pro Phe Ser Asp Pro
            595                 600                 605

Val Pro Tyr Leu Glu Val Pro Val Pro Arg Gly Pro Pro Ser Pro Gly
            610                 615                 620

Asn Pro
625

(2) INFORMATION FOR SEQ ID NO: 49:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO: 49

Met Asp Trp Thr Trp Arg Val Leu Cys Leu Leu Ala Val Ala Pro Gly
1               5                   10                  15

Ala His Ser
        19

(2) INFORMATION FOR SEQ ID NO: 50:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: polypeptide
```

-continued

```
    (xi) SEQUENCE DESCRIPTION: SEQ ID NO: 50

Met Gly Trp Ser Trp Val Met Leu Phe Leu Leu Ser Val Thr Ala Gly
1               5                   10                  15

Lys Gly Leu
        19
```

DELIVERY OF PHARMACEUTICAL AGENTS VIA THE HUMAN INSULIN RECEPTOR

CROSS-REFERENCE TO RELATED APPLICATIONS

This application is a divisional of U.S. patent application Ser. No. 10/307,276, filed Nov. 27, 2002 now U.S. Pat. No. 7,388,079, the specification of which is incorporated herein in its entirety.

BACKGROUND OF THE INVENTION

1. Field of the Invention

The present invention relates generally to the delivery of pharmaceutical agents from the blood stream to the human brain and other organs or tissues that express the human insulin receptor. More particularly, the present invention involves the development of "humanized" monoclonal antibodies (MAb) that may be attached to pharmaceutical agents to form compounds that are able to readily bind to the human insulin receptor (HIR). The compounds are able to cross the human blood brain barrier (BBB) by way of insulin receptors located on the brain capillary endothelium. Once across the BBB, the humanized monoclonal antibody/pharmaceutical agent compounds are also capable of undergoing receptor mediated endocytosis into brain cells via insulin receptors located on the brain cells.

2. Description of Related Art

The publications and other reference materials referred to herein to describe the background of the invention and to provide additional detail regarding its practice are hereby incorporated by reference. For convenience, the reference materials are identified by author and date and grouped in the appended bibliography.

The BBB is a system-wide membrane barrier that prevents the brain uptake of circulating drugs, protein therapeutics, antisense drugs, and gene medicines. Drugs or genes can be delivered to the human brain for the treatment of serious brain disease either (a) by injecting the drug or gene directly into the brain, thus bypassing the BBB, or (b) by injecting the drug or gene into the bloodstream so that the drug or gene enters the brain via the transvascular route across the BBB. With intra-cerebral administration of the drug, it is necessary to drill a hole in the head and perform a procedure called craniotomy. In addition to being expensive and highly invasive, this craniotomy based drug delivery to the brain approach is ineffective, because the drug or gene is only delivered to a tiny volume of the brain at the tip of the injection needle. The only way the drug or gene can be distributed widely in the brain is the transvascular route following injection into the bloodstream. However, this latter approach requires the ability to undergo transport across the BBB. The BBB has proven to be a very difficult and stubborn barrier to traverse safely.

Prior work has shown that drugs or gene medicines can be ferried across the BBB using molecular Trojan horses that bind to BBB receptor/transport systems. These Trojan horses may be modified proteins, endogenous peptides, or peptidomimetic monoclonal antibodies (MAb's). For example, HIR MAb 83-14 is a murine MAb that binds to the human insulin receptor (HIR). This binding triggers transport across the BBB of MAb 83-14 (Pardridge et al, 1995), and any drug or gene payload attached to the MAb (Wu et al., 1997).

The use of molecular Trojan horses to ferry drugs or genes across the BBB is described in U.S. Pat. Nos. 4,801,575 and 6,372,250. The linking of drugs to MAb transport vectors is facilitated with use of avidin-biotin technology. In this approach, the drug or protein therapeutic is monobiotinylated and bound to a conjugate of the antibody vector and avidin or streptavidin. The use of avidin-biotin technology to facilitate linking of drugs to antibody-based transport vectors is described in U.S. Pat. No. 6,287,792. Fusion proteins have also been used where a drug is genetically fused to the MAb transport vector.

HIRMAb 83-14 has been shown to rapidly undergo transport across the BBB of a living Rhesus monkey, and to bind avidly to isolated human brain capillaries, which are the anatomical substrate of the human BBB (see Pardridge et al., 1995). In either case, the activity of the HIRMAb 83-14 with respect to binding and transport at the primate or human BBB is more than 10-fold greater than the binding or transport of other peptidomimetic MAb's that may target other BBB receptors such as the transferrin receptor (Pardridge, 1997). To date, HIRMAb 83-14 is the most active BBB transport vector known (Pardridge, 1997). On this basis, the HIRMAb 83-14 has proven to be a very useful agent for the delivery of drugs to the primate brain in vivo, and would also be highly active for brain drug or gene delivery to the brain in humans.

HIRMAb 83-14 cannot be used in humans because this mouse protein will be immunogenic. Genetically engineered forms of HIRMAb 83-14 might be used in humans in either the form of a chimeric antibody or a genetically engineered "humanized" HIRMAb. However, in order to perform the genetic engineering and production of either a chimeric or a humanized antibody, it is necessary to first clone the variable region of the antibody heavy chain (VH) and the variable region of the antibody light chain (VL). Following cloning of the VH and VL genes, the genes must be sequenced and the amino acid sequence deduced from the nucleotide sequence. With this amino acid sequence, using technologies known to those skilled in the art (Foote et al., 1992), it may be possible to perform humanization of the murine HIRMAb 83-14. However, HIRMAb 83-14 may lose biological activity following the humanization (Pichla et al., 1997). Therefore, it is uncertain as to whether the murine HIRMAb can be humanized with retention of biological activity.

A chimeric form of the HIRMAb 83-14 has been genetically engineered, and the chimeric antibody binds to the HIR and is transported into the primate brain (Coloma et al., 2000). However, a chimeric antibody retains the entire mouse FR for both the VH and the VL, and because of this, chimeric antibodies are still immunogenic in humans (Bruggemann et al., 1989). In contrast to the chimeric antibody, a humanized antibody would use the human FR amino acid sequences for both the VH and the VL and retain only the murine amino acids for the 3 complementarity determining regions (CDR's) of the VH and 3 CDR's of the VL. Not all murine MAb's can be humanized, because there is a loss of biological activity when the murine FR's are replaced by human FR sequences (Pichla et al., 1997). The biological activity of the antibody can be restored by substituting back certain mouse FR amino acids (see U.S. Pat. No. 5,585,089). Nevertheless, even with FR amino acid back-substitution, certain antibodies cannot be humanized with retention of biological activity (Pichla et al., 1997). Therefore, there is no certainty that the murine HIRMAb 83-14 can be humanized even once the key murine CDR and FR amino acid sequences are known.

SUMMARY OF THE INVENTION

In accordance with the present invention, it was discovered that the murine HIRMAb 83-14 antibody can be humanized to provide a biologically active humanized insulin receptor (HIR) antibody that may be used in combination with drugs and diagnostic agents to treat human beings in vivo. The HIR antibody may be conjugated to the drug or diagnostic agent using avidin-biotin conjugation or the HIR antibody/drug combination may be prepared as a fusion protein using genetic engineering techniques. The HIR antibody is especially well suited for delivering neuropharmaceutical agents to the human brain across the BBB. The humanized character of the HIR antibody significantly reduces immunogenic reactions in humans.

The humanized murine antibody of the present invention is capable of binding to the HIR and includes a heavy chain (HC) of amino acids and a light chain (LC) of amino acids which both include variable and constant regions. The variable regions of the HC and LC include complementarity determining regions (CDRs) that are interspersed between framework regions (FRs).

The HC includes a first CDR located at the amino end of the variable region, a third CDR located at the carboxyl end of the HC variable region and a second CDR located between said first and third CDRs. The amino acid sequence for the first CDR is SEQ. ID. NO. 31 and equivalents thereof, the amino acid sequence for the second CDR is SEQ. ID. NO. 33 and equivalents thereof and the amino acid sequence for the third CDR is SEQ. ID. NO. 35 and equivalents thereof. The HC framework regions include a first FR located adjacent to the amino end of the first CDR, a second FR located between said first and second CDRs, a third FR located between said second and third CDRs and a fourth FR located adjacent to the carboxyl end of said third CDR. In accordance with the present invention, the four FRs of the HC are humanized such that the overall antibody retains biological activity with respect to the HIR and is not immunogenic in humans.

The LC also includes a first CDR located at the amino end of the variable region, a third CDR located at the carboxyl end of the variable region and a second CDR located between said first and third CDRs. The amino acid sequence for the first CDR is SEQ. ID. NO. 38 and equivalents thereof, the amino acid sequence for the second CDR is SEQ. ID. NO. 40 and equivalents thereof and the amino acid sequence for the third CDR is SEQ. ID. NO. 42 and equivalents thereof. The LC framework regions include a first FR located adjacent to the amino end of said first CDR, a second FR located between said first and second CDRs, a third FR located between said second and third CDRs and a fourth FR located adjacent to the carboxyl end of said third CDR. Pursuant to the present invention, the four FRs of the LC are humanized such that the overall antibody retains biological activity with respect to the HIR and has minimal immunogenicity in humans.

The constant regions of the murine antibody are also modified to minimize immunogenicity in humans. The murine HC constant region is replaced with the HC constant region from a human immunoglobulin such as IgG1. The murine LC constant region is replaced with a constant region from the LC of a human immunoglobulin such as a κ LC constant region. Replacement of the murine HC and LC constant regions with human constant regions was found to not adversely affect the biological activity of the humanized antibody with respect to HIR binding.

The present invention not only covers the humanized murine antibodies themselves, but also covers pharmaceutical compositions that are composed of the humanized antibody linked to a drug or diagnostic agent. The humanized antibody is effective in delivering the drug or diagnostic agent to the HIR in vivo to provide transport across the BBB and/or endocytosis into cells via the HIR. The compositions are especially well suited for intra venous (iv.) injection into humans for delivery of neuropharmaceutical agents to the brain.

The above discussed and many other features and attendant advantages of the present invention will become better understood by reference to the detailed description when taken in conjunction with the accompanying drawings.

BRIEF DESCRIPTION OF THE DRAWINGS

FIG. 1 shows the nucleotide sequence for the murine VH (SEQ. ID. NO. 1) and murine VL (SEQ. ID. NO. 2) and deduced amino acid sequence of the murine VH (SEQ. ID. NO. 3) and the murine VL (SEQ. ID. NO. 4), which shows the 3 framework (FR) regions and the 4 complementarity determining regions (CDRs) of both the heavy chain (HC) and the light chain (LC) of the 83-14 murine HIRMAb. The amino acids denoted by an asterisk (*) were confirmed by amino acid sequencing of either the intact murine LC or tryptic peptides of the intact murine HC; for amino acid sequencing, the intact murine HC or LC were purified from gels following purification of the intact murine IgG from the hybridoma conditioned medium.

FIG. 4 shows a comparison of the amino acid sequence for the 3 FRs and 3 CDRs of both the heavy chain and the light chain for the following: (a) the version 5 humanized HIRMAb, (v) the original murine 83-14 HIRMAb, and (c) the VH of the B43 human IgG or the VL of the REI human IgG.

DETAILED DESCRIPTION OF THE INVENTION

Figure 2:
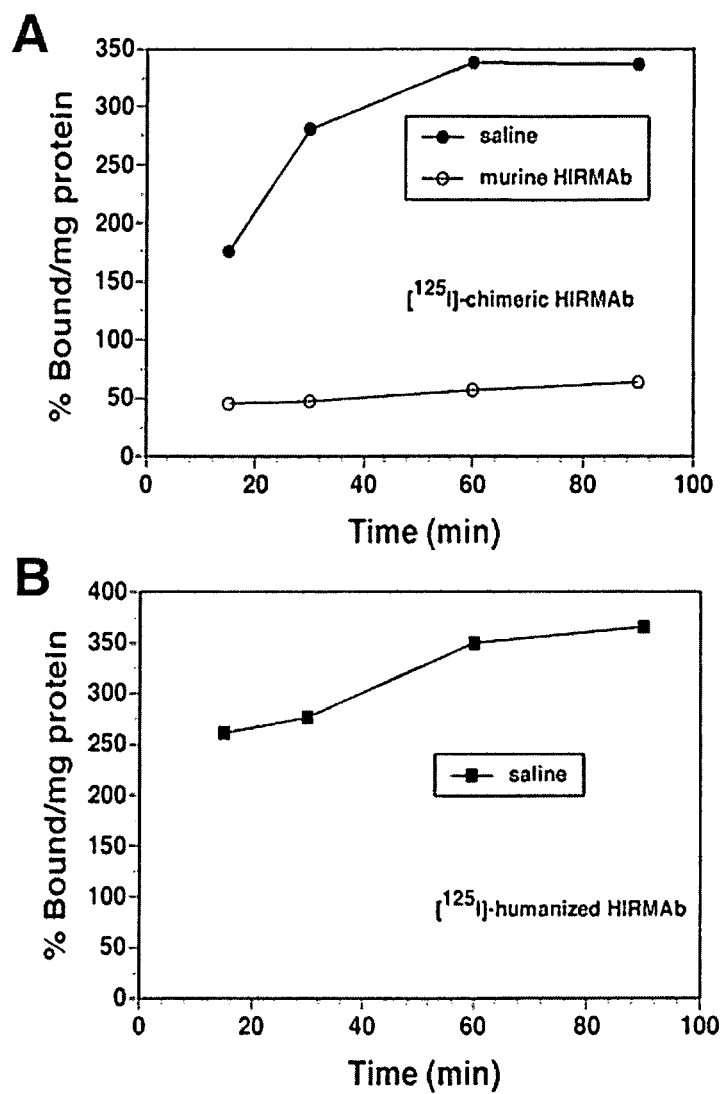
FIGS. 2A and 2B graphically show the results of a radio-receptor assay on isolated human brain capillaries that were obtained with a mechanical homogenization procedure from human autopsy brain. These capillaries were incubated with [$^{125}$I]-labeled chimeric HIRMAb (Coloma et al., 2000) (FIG. 2A) or [$^{125}$I]-version 5 humanized HIRMAb (FIG. 2B). The data show that both antibodies bind equally well to human brain capillaries, which form the anatomical basis of the BBB in humans.

The present invention involves the humanization of the murine monoclonal antibody identified as MAb 83-14 so that it can be used in vivo in humans. As previously mentioned, MAb 83-14 has a high affinity for the human insulin receptor at the human or rhesus monkey blood-brain barrier (Pardridge, et al. 1995) and is a candidate for use as a Trojan horse to transport neuropharmaceutical agents across the BBB. As used herein, the term "pharmaceutical agents" is intended to include any drug, gene or chemical that is used to treat or diagnose disease in humans. The term "neuropharmaceutical agent" covers pharmaceutical agents that are used to treat brain disease. The present humanized antibody Trojan horses are especially well-suited for transporting neuropharmaceutical agents from the blood stream to the brain across the BBB.

The complete amino acid sequence for the variable region of the HC and LC of murine Mab 83-14 was determined as described in Example 1. The nucleotide sequence for the gene that expresses the murine VH (SEQ. ID. NO. 1) and the murine VL (SEQ. ID. NO. 2) is set forth in FIG. 1. The amino acid sequence for the murine VH (SEQ. ID. NO. 3) and murine VL (SEQ. ID. NO. 4) is also set forth in FIG. 1. The amino acid sequences for the variable regions of the murine MAb 83-14 VH and VL are also set forth in FIG. 4 (SEQ. ID. NOS. 3 AND 4, respectively). The humanized murine antibodies of the present invention are prepared by modifying the amino acid sequences of the variable regions of the murine antibody to more closely resemble human antibody without destroying the ability of the antibody to strongly bind to the HIR. In addition, the humanized antibody includes constant regions that also correspond to human antibody.

The humanized murine antibodies include a heavy chain of amino acids (HC) that is composed of a constant region (CH) and a variable region (VH). The variable region of the HC has an amino end and a carboxyl end and includes three CDRs interspersed between four FRs. The first CDR (CDR1) is located towards the amino end of the VH with the third CDR (CDR3) being located towards the carboxyl end of the HC. The amino acid sequences for murine MAb 83-14 HC CDR1, CDR2, and CDR3 are set forth in SEQ. ID. NOS. 31, 33 and 35, respectively. Since the HC CDRs are essential for antibody binding to the HIR, it is preferred that the humanized antibodies have HC CDRs with amino acid sequences that are identical to SEQ. ID. NOS. 31, 33 and 35. However, the humanized antibodies may include CDRs in the HC that have amino acid sequences which are "individually equivalent" to SEQ. ID. NOS. 31, 33 and 35. "Individually Equivalent" amino acid sequences are those that have at least 75 percent sequence identity and which do not adversely affect the binding of the antibody to the HIR. Preferably, individually equivalent amino acid sequences will have at least 85 percent sequence identity with SEQ. ID. NOS. 31, 33 or 35. Even more preferred are individually equivalent amino acid sequences having at least 95 percent sequence identity.

The three VH CDR amino acid sequences may also be viewed as a combined group of amino acid sequences (VH CDR1, VH CDR2 and VH CDR3). The present invention also covers equivalents of the combined group of VH CDR sequences. Such "combined equivalents" are those that have at least 75 percent sequence identity with the combined amino acid sequences SEQ. ID. NOS. 31, 32 and 35 and which do not adversely affect the binding of the antibody to the HIR. Preferably, combined equivalent amino acid sequences will have at least 85 percent sequence identity with the combined sequences found in SEQ. ID. NOS. 31, 33 and 35. Even more preferred are combined equivalent amino acid sequences that have at least 95 percent sequence identity with the combined amino acid sequences (SEQ. ID. NOS. 31, 33 and 35).

It is preferred that the VH CDR amino acid sequences meet both the individual equivalency and combined equivalency requirements set forth above. However, there are certain situations, especially for the shorter CDR's, where one or more of the CDR's may not meet the criteria for individual equivalence eventhough the criteria for combined equivalence is met. In such situations, the individual equivalency requirements are waived provided that the combined equivalency requirements are met For example, VH CDR3 (SEQ. ID. NO. 35) is only 4 amino acids long. If two amino acids are changed, then the individual sequence identity is only 50% which is below the 75% floor for individual equivalence set forth above. However, this particular sequence is still suitable for use as part of a combined equivalent VH CDR group provided that the sequence identity of the combined CDR1, CDR2 and CDR3 sequences meet the group equivalency requirements.

The humanized murine antibodies also include a light chain (LC) of amino acids that is composed of a constant region (CL) and a variable region (VL). The variable region of the LC has an amino end and a carboxyl end and includes three CDRs interspersed between four FRs. The first CDR (CDR1) is located towards the amino end of the VL with the third CDR (CDR3) being located towards the carboxyl end of the VL. The amino acid sequences for murine MAb 83-14 LC CDR1, CDR2, and CDR3 are set forth in SEQ. ID. NOS. 38, 40 and 42, respectively. Since the VL CDRs are also important for antibody binding to the HIR, it is preferred that the humanized antibodies have LC CDRs with amino acid sequences that are identical to SEQ. ID. NOS. 38, 40 and 42. However, the humanized antibodies may include CDRs in the VL that have amino acid sequences which are "individually equivalent" to SEQ. ID. NOS. 38, 40 or 42. "Individually equivalent" amino acid sequences are those that have at least 75 percent sequence identity and which do not adversely affect the binding of the antibody to the HIR. Preferably, individually equivalent amino acid sequences will have at least 85 percent sequence identity with SEQ. ID. NOS. 38, 40 or 42. Even more preferred are individually equivalent amino acid sequences having at least 95 percent sequence identity.

The three VL CDR amino acid sequences may also be viewed as a combined group of amino acid sequences (VL CDR1, VL CDR2 and VL CDR3). The present invention also covers equivalents of the combined group of VL CDR sequences. Such "combined equivalents" are those that have at least 75 percent sequence identity with the combined amino acid sequences SEQ. ID. NOS. 38, 40 and 42 and which do not adversely affect the binding of the antibody to the HIR. Preferably, combined equivalent amino acid sequences will have at least 85 percent sequence identity with the combined sequences found in SEQ. ID. NOS. 38, 40 and 42. Even more preferred are combined equivalent amino acid sequences that have at least 95 percent sequence identity with the combined amino acid sequences (SEQ. ID. NOS. 38, 40 and 42).

It is preferred that the VL CDR amino acid sequences meet both the individual equivalency and combined equivalency requirements set forth above. However, there are certain situations, especially for the shorter CDR's, where one or more of the CDR's may not meet the criteria for individual equivalence eventhough the criteria for combined equivalence is met. In such situations, the individual equivalency requirements are waived provided that the combined equivalency requirements are met. For example, VH CDR3 (SEQ. ID. NO. 42) is only 9 amino acids long. If three amino acids are changed, then the individual sequence identity is only 66% which is below the 75% floor for individual equivalence set forth above. However, this particular sequence is still suitable for use as part of a combined equivalent VL CDR group provided that the sequence identity of the combined CDR1, CDR2 and CDR3 sequences meet the group equivalency requirements.

The first framework region (FR1) of the VH is located at the amino end of the humanized antibody. The fourth framework region (FR4) is located towards the carboxyl end of the humanized antibody. Exemplary preferred amino acid sequences for the humanized VH FR1, FR2, FR3 and FR4 are set forth in SEQ. ID. NOS. 30, 32, 34 and 36, respectively, and these preferred sequences correspond to version 5 humanized HIRMAb (Table 3). The amino acid sequence for FR2 (SEQ. ID. NO. 32) is identical to the amino acid sequence of murine MAb 83-14 VH FR2 or the human IgG, B43 (See FIG. 4). The amino acid sequences for VH FR1 and FR4 (SEQ. ID. NOS. 30 and 36) correspond to the B43 human antibody framework regions that have amino acid sequences that differ from murine MAb 83-14 (FIG. 4). The amino acid sequences for the VH FR3 (SEQ. ID. No. 34) of the version 5 humanized HIRMAb corresponds to the VH FR3 of the murine 83-14 antibody (Table 3). It is possible to modify the preferred VH FR sequences without destroying the biological activity of the antibody. Suitable alternate or equivalent FRs include those that have at least 70 percent individual sequence identity with SEQ. ID. NOS. 30, 32, 34 or 36 and do not destroy the resulting antibodies ability to bind the HIR. Preferably, the alternate FRs will have at least 80 percent sequence identity with the preferred VH FR that is being replaced. Even more preferred are alternate FRs that have at least 90 percent sequence identity with the preferred VH FR that is being replaced.

The four VH FR amino acid sequences may also be viewed as a combined group of amino acid sequences (VH FR1, VH FR2, VH FR3 and VH FR4). The present invention also covers alternates or equivalents of the combined group of VH FR sequences. Such "combined equivalents" are those that have at least 70 percent sequence identity with the combined amino acid sequences SEQ. ID. NOS. 30, 32, 34 and 36 and which do not adversely affect the binding of the antibody to the HIR. Preferably, combined equivalent amino acid sequences will have at least 80 percent sequence identity with the combined sequences found in SEQ. ID. NOS. 30, 32, 34 and 36. Even more preferred are combined equivalent amino acid sequences that have at least 90 percent sequence identity with the combined amino acid sequences (SEQ. ID. NOS. 30, 32, 34 and 36).

It is preferred that the alternate VH FR amino acid sequences meet both the individual equivalency and combined equivalency requirements set forth above. However, there are certain situations, especially for the shorter FR's, where one or more of the FR's may not meet the criteria for individual equivalence even though the criteria for combined equivalence is met. In such situations, the individual equivalency requirements are waived provided that the combined equivalency requirements are met.

The first framework region (FR1) of the LC is located at the amino end of the VL of the humanized antibody. The fourth framework region (FR4) is located towards the carboxyl end of the VL of the humanized antibody. Exemplary preferred amino acid sequences for the humanized VL FR1, FR2, FR3 and FR4 are set forth in SEQ. ID. NOS. 37, 39, 41 and 43, respectively. The amino acid sequences for LC FR1, FR2, FR3 and FR4 (SEQ. ID. NOS. 37, 39, 41 and 43) correspond to the REI human antibody framework regions that have amino acid sequences that differ from murine MAb 83-14 (See FIG. 4). It is possible to modify the preferred VL FR sequences without destroying the biological activity of the antibody. Suitable alternate or equivalent FRs include those that have at least 70 percent sequence identity with SEQ. ID. NOS. 37, 39, 41 and 43 and do not destroy the resulting antibodies ability to bind the HIR. Preferably, the equivalent or alternate FRs will have at least 80 percent sequence identity with the preferred VL FR that is being replaced. Even more preferred are alternate FRs that have at least 90 percent sequence identity with the preferred VL FR that is being replaced.

The four VL FR amino acid sequences may also be viewed as a combined group of amino acid sequences (VL FR1, VL FR2, VL FR3 and VL FR4). The present invention also covers alternates or equivalents of the combined group of VL FR sequences. Such "combined equivalents" are those that have at least 70 percent sequence identity with the combined amino acid sequences SEQ. ID. NOS. 37, 39, 41 and 43 and which do not adversely affect the binding of the antibody to the HIR. Preferably, combined equivalent amino acid sequences will have at least 80 percent sequence identity with the combined sequences found in SEQ. ID. NOS. 37, 39, 41 and 43. Even more preferred are combined equivalent amino acid sequences that have at least 90 percent sequence identity with the combined amino acid sequences (SEQ. ID. NOS. 37, 39, 41 and 43).

It is preferred that the alternate VL FR amino acid sequences meet both the individual equivalency and combined equivalency requirements set forth above. However, there are certain situations, especially for the shorter FR's, where one or more of the FR's may not meet the criteria for individual equivalence eventhough the criteria for combined equivalence is met. In such situations, the individual equivalency requirements are waived provided that the combined equivalency requirements are met.

Version 5 is a preferred humanized antibody in accordance with the present invention. The amino acid sequences for the VH and VL of Version 5 are set forth in SEQ. ID. NOS. 5 and 6, respectively. The preparation and identification of Version 5 is set forth in more detail in Example 2, Table 3 and FIG. 4. The amino acid sequences for the VH FRs of Version 5 correspond to the preferred VH FR sequences set forth above (SEQ. ID. NOS. 30, 32, 34 and 36). In addition, the amino acid sequences for the VL FRs of Version 5 correspond to the preferred VL FR sequences set forth above (SEQ. ID. NOS. 37, 39, 41, 43). The VH and VL FRs of Version 5 are a preferred example of VH and VL LC FRs that have been "humanized". "Humanized" means that the four framework regions in either the HC or LC have been matched as closely as possible with the FRs from a human antibody (HAb) without destroying the ability of the resulting antibody to bind the HIR. The model human antibody used for the HC is the B43 antibody, and the model human antibody used for the LC is the REI antibody, and both the B43 and REI antibody sequences are well known and available in public databases. When the HC or LC FRs are humanized, it is possible that one or more of the FRs will not correspond identically with the chosen HAb template and may retain identity or similarity to the murine antibody. The degree to which murine amino acid sequences are left in the humanized FRs should be kept as low as possible in order to reduce the possibility of an immunogenic reaction in humans.

Examples of FRs that have been humanized are set forth in Example 2 and Table 3. Framework regions from human antibodies that correspond closely to the FRs of murine MAb 84-13 are chosen. The human FRs are then substituted into the MAb 84-13 in place of the murine FRs. The resulting antibody is then tested. The FRs, as a group, are only considered to be humanized if the modified antibody still binds strongly to the HIR receptor and has reduced immunogenicity in humans. If the first test is not successful, then the human FRs are modified slightly and the resulting antibody tested. Exemplary human antibodies that have HC FRs that may be used to humanize the HC FRs of MAb 84-13 include B43 human IgG (SEQ. ID. NO. 12), which is deposited in Genbank (accession number S78322), and other human IgG molecules with a VH homologous to the murine 83-14 VH may be found by searching public databases, such as the Kabat Database of immunoglobulin sequences. Exemplary human antibodies that have LC FRs that may be used to humanize the LC FRs of MAb 84-13 include human REI antibody (SEQ. ID. NO. 13), which is deposited in Genbank (accession number 1WTLB), and other human IgG molecules with a VL homologous to the murine 83-14 VL may be found by searching public databases, such as the Kabat Database of immunoglobulin sequences.

In order for the humanized antibody to function properly, the HC and LC should each include a constant region. Any number of different human antibody constant regions may be incorporated into the humanized antibody provided that they do not destroy the ability of the antibody to bind the HIR. Suitable human antibody HC constant regions include human IgG1, IgG2, IgG3, or IgG4. The preferred HC constant region is human IgG1. Suitable human antibody LC constant regions include kappa (K) or lambda. Human κ LC constant regions are preferred.

The humanized antibody may be used in the same manner as any of the other antibody targeting agents (Trojan Horses) that have previously been used to deliver genes, drugs and diagnostic agents to cells by accessing the HIR. The humanized antibody is typically linked to a drug or diagnostic compound (pharmaceutical agent) and combined with a suitable pharmaceutical carrier and administered intravenously (iv). With suitable carriers, the drug/humanized antibody complex could also be administered subcutaneously, intra-muscularly, intra-nasally, intra-thecally, or orally. There are a number of ways that the humanized antibody may be linked to the pharmaceutical agent. The humanized antibody may be fused to either avidin or streptavidin and conjugated to a pharmaceutical agent that has been mono-biotinylated in accordance with known procedures that use the avidin-biotin linkage to conjugate antibody Trojan Horses and pharmaceutical agents together. Alternatively, the humanized antibody and pharmaceutical agent may be expressed as a single fusion protein using known genetic engineering procedures.

Exemplary pharmaceutical agents to which the humanized antibody may be linked include small molecules, recombinant proteins, synthetic peptides, antisensense agents or nanocontainers for gene delivery. Exemplary recombinant proteins include basic fibroblast growth factor (bFGF), human α-L-iduronidase (IDUA), or other neurotrophins, such as brain derived neurotrophic factor, or other lysosomal enzymes. The use of Trojan Horses, such as the present humanized antibody, for transporting bFGF across the BBB is described in a co-pending United States Patent Application (UC Case 2002-094-1, Attorney Docket 0180-0027) that is owned by the same assignee as the present application and which was filed on the same day as the present application)

Once the humanized antibody is linked to a pharmaceutical agent, it is administered to the patient in the same manner as other known conjugates or fusion proteins. The particular dose or treatment regimen will vary widely depending upon the pharmaceutical agent being delivered and the condition being treated. The preferred route of administration is intravenous (iv). Suitable carriers include saline or water buffered with acetate, phosphate, TRIS or a variety of other buffers, with or without low concentrations of mild detergents, such as one from the Tween series of detergents. The humanized antibody/pharmaceutical agent Trojan horse compound is preferably used to deliver neuropharmaceutical agents across the BBB. However, the humanized Trojan horse may also be used to deliver pharmaceutical agents, in general, to any organ or tissue that carries the HIR.

The following examples describe how the humanized monoclonal antibodies in accordance with the present invention were discovered and additional details regarding their fabrication and use.

EXAMPLE 1

Cloning of Murine 83-14 VH and VL Genes

Poly A+ RNA was isolated from the 83-14 hybridoma cell line (Soos et al, 1986), and used to produce complementary DNA (cDNA) with reverse transcriptase. The cDNA was used with polymerase chain reaction (PCR) amplification of either the 83-14 VH or 83-14 VL gene using oligodeoxynucleotide (ODN) primers that specifically amplify the VH and VL of murine antibody genes, and similar methods are well known (Li et al., 1999). The sequences of PCR ODNs suitable for PCR amplification of these gene fragments are well known (Li., 1999). The PCR products were isolated from 1% agarose gels and the expected 0.4 Kb VH and VL gene products were isolated. The VH and VL gene fragments were sequentially subcloned into a bacterial expression plasmid so as to encode a single chain Fv (ScFv) antibody. The ScFv expression plasmid was then used to transform *E. Coli*. Individual colonies were identified on agar plates and liquid cultures were produced in LB medium. This medium was used in immunocytochemistry of Rhesus monkey brain to identify clones producing antibody that bound avidly to the Rhesus monkey brain microvasculature or BBB. This immunocytochemistry test identified those colonies secreting the functional 83-14 ScFv. Following identification of the 83-14 VH and VL genes, the nucleotide sequence was determined in both directions using automatic DNA sequencing methods. The nucleotide sequence of the murine 83-14 VH (SEQ. ID. NO. 1) and the murine VL (SEQ. ID. NO. 2) gives the deduced amino acid sequence for the murine VH (SEQ. ID. NO. 3) and the murine VL (SEQ. ID. NO. 4). The amino acid sequence is given for all 3 CDRs and all 4 FRs of both the HC and the LC of the murine 83-14 HIRMAb. The variable region of the LC is designated VL, and the variable region of the HC is designated VH in FIG. 1.

EXAMPLE 2

Iterative Humanization of the 83-14 HIRMAb: Version 1 through Version 5

Humanization of the 83-14 MAb was performed by CDR/FR grafting wherein the mouse FRs in the 83-14 MAb are replaced by suitable human FR regions in the variable regions of both the LC and HC. The Kabat database was screened using the Match program. Either the murine 83-14 VH or the VL amino acid sequence was compared with human IgG VH or human K light chain VL databases. Using the minimal mismatch possible, several human IgG molecules were identified that contained FR amino sequences highly homologous to the amino acid sequences of the murine 83-14 VH and VL. The framework regions of the B43 human IgG1 heavy chain and the REI human K light chain were finally selected for CDR/FR grafting of the murine 83-14 HIRMAb.

Sets of 6 ODN primers, of 69-94 nucleotides in length, were designed to amplify the synthetic humanized 83-14 VL and VH genes (Tables 1 and 2). The ODN primers overlapped 24 nucleotides in both the 5'- and 3'-ends, and secondary structure was analyzed with standard software. Stable secondary structure producing $T_m$ of >46° C. was corrected by replacement of first, second, or third letter codons to reduce the melting point of these structures to 32-46° C. In addition, primers corresponding to both 5' and 3' ends were also designed, and these allowed for PCR amplification of the artificial genes. These new sequences lack any consensus N-glycosylation sites at asparagine residues.

TABLE 1

Oligodeoxynucleotides for CDR/FR grafting of VL

Primer 1 FWD

5'TAGGATATCCACCATGGAGACCCCCGCCCAGCTGCTGTTCCTGTTGCT

GCTTTGGCTTCCAGATACTACCGGTGACATCCAGATGACCCAG-3'
(SEQ. ID. NO. 14)

Primer 2 reverse

5'GTCCTGACTAGCCCGACAAGTAATGGTCACTCTGTCACCCACGCTGGC

GCTCAGGCTGCTTGGGCTCTGGGTCATCTGGATGTCGCCGGT-3'
(SEQ. ID. NO. 15)

Primer 3 FWD

5'ATTACTTGTCGGGCTAGTCAGGACATTGGAGGAAACTTATATTGGTAC

CAACAAAAGCCAGGTAAAGCTCCAAAGTTACTGATCTACGCC-3'
(SEQ. ID. NO. 16)

Primer 4 reverse

5'GGTGTAGTCGGTACCGCTACCACTACCACTGAATCTGCTTGGCACACC

AGAATCTAAACTAGATGTGGCGTAGATCAGTAACTTTGGAGC-3'
(SEQ. ID. NO. 17)

Primer 5 FWD

5'AGTGGTAGCGGTACCGACTACACCTTCACCATCAGCAGCTTACAGCCA

GAGGACATCGCCACCTACTATTGCCTACAGTATTCTAGTTCT-3'
(SEQ. ID. NO. 18)

Primer 6 reverse

5'CCCGTCGACTTCAGCCTTTTGATTTCCACCTTGGTCCCTTGTCCGAAC

GTCCATGGAGAACTAGAATACTGTAGGCAATA-3'
(SEQ. ID. NO. 19)

5-PCR primer FWD

5'TAGGATATCCACCATGGAGACCCC-3'
(SEQ. ID. NO. 20)

3-PCR primer reverse

5'CCCGTCGACTTCAGCCTTTTGATT-3'
(SEQ. ID. NO. 21)

TABLE 2

Oligodeoxynucleotides for CDR/FR grafting of VH

PRIMER 1 FWD

5'TAGGATATCCACCATGGACTGGACCTGGAGGGTGTTATGCCTGCTTGC

AGTGGCCCCCGGAGCCCACAGCCAAGTGCAGCTGCTCGAGTCTGGG-3'
(SEQ. ID. NO. 22)

PRIMER 2 REVERSE

5'GTTTGTGAAGGTGTAACCAGAAGCCTTGCAGGAAATCTTCACTGAGGA

CCCAGGCCTCACCAGCTCAGCCCCAGACTCGAGCAGCTGCACTTG-3'
(SEQ. ID. NO. 23)

PRIMER 3 FWD

5'GCTTCTGGTTACACCTTCACAAACTACGATATACACTGGGTGAAGCAG

AGGCCTGGACAGGGTCTTGAGTGGATTGGATGGATTTATCCTGGA-3'
(SEQ. ID. NO. 24)

PRIMER 4 REVERSE

5'GCTGGAGGATTCGTCTGCAGTCAGAGTGGCTTTGCCCTTGAATTTCTC

ATTGTACTTAGTACTACCATCTCCAGGATAAATCCATCCAATCCA-3'
(SEQ. ID. NO. 25)

PRIMER 5 FWD

5'CTGACTGCAGACGAATCCTCCAGCACAGCCTACATGCAACTAAGCAGC

CTACGATCTGAGGACTCTGCGGTCTATTCTTGTGCAAGAGAGTGG-3'
(SEQ. ID. NO. 26)

PRIMER 6 REVERSE

5'CATGCTAGCAGAGACGGTGACTGTGGTCCCTTGTCCCCAGTAAGCCCA

CTCTCTTGCACAAGAATAGAC-3'
(SEQ. ID. NO. 27)

5'-PCR PRIMER FWD

5'TAGGATATCCACCATGGACTGGACCTG-3'
(SEQ. ID. NO. 28)

3'-PRC PRIMER REV

5'CATGCTAGCAGAGACGGTGACTGTG-3'
(SEQ. ID. NO. 29)

The PCR was performed in a total volume of 100 μL containing 5 pmole each of 6 overlapping ODNs, nucleotides, and Taq and Taq extender DNA polymerases. Following PCR, the humanized VH and VL genes were individually ligated in a bacterial expression plasmid and *E. coli* was transformed. Several clones were isolated, individually sequenced, and clones containing no PCR-introduced sequence errors were subsequently produced.

The humanized VH insert was released from the bacterial expression plasmid with restriction endonucleases and ligated into eukaryotic expression vectors described previously (Coloma et al, 1992; U.S. Pat. No. 5,624,659). A similar procedure was performed for the humanized VL synthetic gene. Myeloma cells were transfected with the humanized light chain gene, and this cell line was subsequently transfected with version 1 of the humanized heavy chain gene (Table 3). The transfected myeloma cells were screened in a 96-well ELISA to identify clones secreting intact human IgG. After multiple attempts, no cell lines producing human IgG could be identified. Conversely, Northern blot analysis indicated the transfected cell lines produced the expected humanized 83-14 mRNA, which proved the transfection of the cell line was successful. These results indicated that version 1 of the humanized HIRMAb, which contains no FR amino acid substitutions, was not secreted from the cell, and suggested the humanized HC did not properly assemble with the humanized LC. Version 1 was derived from a synthetic HC gene containing FR amino acids corresponding to the 25C1'Cl antibody (Bejcek et al, 1995). Therefore, a new HC artificial gene was prepared, which contained HC FR amino acids derived from a different human IgG sequence, that of the B43 human IgG (Bejcek et al, 1995), and this yielded version 2 of the humanized HIRMAb (Table 3). However, the version 2 humanized HIRMAb was not secreted by the transfected myeloma cell. Both versions 1 and 2 contain the same HC signal peptide (Table 3), which is derived from Rechavi et al (1983). In order to evaluate the effect of the signal peptide on IgG secretion, the signal peptide sequence was changed to that used for production of the chimeric HIRMAb (Coloma et al, 2000), and the sequence of this signal peptide is given in Table 3. Versions 2 and 3 of the humanized HIRMAb differed only with respect to the signal peptide (Table 3). However, version 3 was not secreted from the myeloma cell, indicating the signal peptide was not responsible for the lack of secretion of the humanized HIRMAb.

The above findings showed that simply grafting the murine 83-14 CDRs on to human FR regions produced a protein that could not be properly assembled and secreted. Prior work had shown that the chimeric form of the HIRMAb was appropriately processed and secreted in transfected myeloma lines (Coloma et al, 2000). This suggested that certain amino acid sequences within the FRs of the humanized HC or LC prevented the proper assembly and secretion of the humanized HIRMAb. Therefore, chimeric/humanized hybrid molecules were engineered. Version 4a contained the murine FR1 and the humanized FR2, FR3, and FR4; version 4b contained the murine FR 3, and FR4 and the humanized FR1 and FR2 (Table 3). Both versions 4a and 4b were secreted, although version 4b was more active than version 4a. These findings indicated amino acids within either FR3 or FR4 were responsible for the lack of secretion of the humanized HIRMAb. The human and murine FR4 differed by only 1 amino acid (Table 3); therefore, the sequence of FR4 was altered by site-directed mutagenesis to correspond to the human sequence, and this version was designated version 5 (Table 3). The version 5 HIRMAb corresponded to the original CDR-grated antibody sequence with substitution of the human sequence in FR3 of the VH with the original murine sequence for the FR3 in the VH. The same CDR-grafted LC, without any FR substitutions, was used in production of all versions of the humanized HIRMAb. This corresponds with other work showing no FR changes in the LC may be required (Graziano et al, 1995).

TABLE 3

Iterations of Genetic Engineering of Humanized HIRMAb Heavy Chain

|  | FR1 | CDR1 | FR2 |
|---|---|---|---|
| Version 5 | QVQLLESGAELVRPGSSVKISCKAS | GYTFTNYDIH | WVKQRPGQGLEWIG |
| Version 4b | QVQLLESGAELVRPGSSVKISCKAS | GYTFTNYDIH | WVKQRPGQGLEWIG |
| Version 4a | QVQLQESGPELVKPGALVKISCKAS | GYTFTNYDIH | WVKQRPGQGLEWIG |
| Version 3 | QVQLLESGAELVRPGSSVKISCKAS | GYTFTNYDIH | WVKQRPGQGLEWIG |
| Version 2 | QVQLLESGAELVRPGSSVKISCKAS | GYTFTNYDIH | WVKQRPGQGLEWIG |
| Version 1 | QVQLLESGAELVRPGSSVKISCKAS | GYTFTNYDIH | WVKQRPGQGLEWTG |
| murine | QVQLQESGPELVKPGALVKISCKAS | GYTFTNYDIH | WVKQRPGQGLEWIG |
| human B43 | QVQLLESGAELVRPGSSVKISCKAS | GYAFSSYWMN | WVKQRPGQGLEWIG |
|  | 1 | 26 | 36 |

|  | CDR2 | FR3 |
|---|---|---|
| Version 5 | WIYPGDGSTKYNEKFKG | KATLTADKSSSTAYMHLSSLTSEKSAVYFCAR |
| Version 4b | WIYPGDGSTKYNEKFKG | KATLTADKSSSTAYMHLSSLTSEKSAVYFCAR |
| Version 4a | WIYPGDGSTKYNEKFKG | KATLTADESSSTAYMQLSSLRSEDSAVYSCAR |
| Version 3 | WIYPGDGSTKYNEKFKG | KATLTADESSSTAYMQLSSLRSEDSAVYSCAR |
| Version 2 | WIYPGDGSTKYNEKFKG | KATLTADESSSTAYMQLSSLRSEDSAVYSCAR |
| Version 1 | WIYPGDGSTKYNEKFKG | QATLTADKSSSTAYMQLSSLTSEDSAVYSCAR |
| murine | WIYPGDGSTKYNEKFKG | KATLTADKSSSTAYMHLSSLTSEKSAVYFCAR |
| human B43 | QIWPGDGDTNYNGKFKG | KATLTADESSSTAYMQLSSLRSEDSAVYSCAR |
|  | 50 | 67 |

|  | CDR3 | FR4 |  |
|---|---|---|---|
| Version 5 | -----------EWAY | WGQGTTVTVSA | (SEQ. ID. NO. 5) |
| Version 4b | -----------EWAY | WGQGTLVTVSA | (SEQ. ID. NO. 11) |
| Version 4a | -----------EWAY | WGQGTTVTVSA | (SEQ. ID. NO. 10) |
| Version 3 | -----------EWAY | WGQGTTVTVSA | (SEQ. ID. NO. 9) |
| Version 2 | -----------EWAY | WGQGTTVTVSA | (SEQ. ID. NO. 8) |
| Version 1 | -----------EWAY | WGQGTTVTVSA | (SEQ. ID. NO. 7) |
| murine | -----------EWAY | WGQGTLVTVSA | (SEQ. ID. NO. 3) |
| human B43 | RETTTVGRYYYAMDY | WGQGTTVT--- | (SEQ. ID. NO. 12) |
|  | 99          99 | 103    113 |  |

Version 1 was designed using the FRs of the human 25ClCl IgG heavy chain (HC) variable region (VH). Version 1 did not produce secreted hIgG from the transfected myeloma cells despite high abundance of the HC mRNA determined by Northern blot analysis.

Version 2 was re-designed using the FRs of the human B43 IgG HC variable region. The peptide signal #1 (MDWTWRVLCLLAVAPGAHS) (SEQ. ID. NO. 49) in versions 1 and 2 was replaced by signal peptide #2 (MGWSWVMLFLLSVTAGKGL) (SEQ. ID. NO. 50) in version 3. The FRs and CDRs in version 2 and 3 are identical. The signal peptide #2 was used for versions 4a, 4b and 5.

Version 4a has human FRs 2, 3 and 4 and murine FR1.

Version 4b has human FRs 1 and 2, and murine FRs 3 and 4

Version 5 was produced using the human FRs 1, 2 and 4 and the murine FR3.

Versions 4a, 4b and 5 produced secreted hIgG, whereas version 1, 2, and 3 did not secrete IgG. Among versions 4a, 4b, and 5, version 5 contains fewer murine framework amino acid substitutions and is preferred.

The version 5 form of the protein was secreted intact from the transfected myeloma lines. The secreted version 5 humanized HIRMAb was purified by protein A affinity chromatography and the affinity of this antibody for the HIR was tested with an immunoradiometric assay (IRMA), which used [$^{125}$I]-labeled murine 83-14 MAb as the ligand as described previously (Coloma et al, 2000). These results showed that the affinity of the antibody for the HIR was retained. In the IRMA, the antigen was the extracellular domain of the HR, which was produced from transfected CHO cells and purified by lectin affinity chromatography of CHO cell conditioned medium. The dissociation constant ($K_D$) of the murine and Version 5 humanized 83-14 HIRMAb was 2.7±0.4 nM and 3.7±0.4 nM, respectively. These results show that the 83-14 HIRMAb has been successfully humanized using methods that (a) obtain the FR regions of the HC and of the LC from different human immunoglobulin molecules, and (b) do not require the use of molecular modeling of the antibody structure, as taught in U.S. Pat. No. 5,585,089. Similar to other applications (Graziano et al., 1995), no FR amino acid changes in the LC of the antibody were required.

EXAMPLE 3

Binding of the Humanized HIRMAb to the Human BBB

Prior work has reported that the radiolabelled murine HIRMAb avidly binds to human brain capillaries with percent binding approximately 400% per mg protein at 60-120 minutes of incubation (Pardridge et al., 1995). Similar findings were recorded with radiolabelled Version 5 humanized HIRMAb in this example. When human brain capillaries were incubated in a radioreceptor assay with [$^{125}$I] Version 5 humanized HIRMAb, the percent binding approximated 400% per mg protein by 60 minutes of incubation at room temperature, and approximated the binding to the human brain capillary of the [$^{125}$I-chimeric HIRMAb (see FIGS. 2A and 2B). In contrast, the binding of a nonspecific IgG to human brain capillaries is less than 5% per mg protein during a comparable incubation period Pardridge et al., 1995). This example shows that the Version 5 humanized HIRMAb was avidly bound and endocytosed by the human brain capillary, which forms the BBB in vivo.

EXAMPLE 4

Transport of Humanized HIRMAb Across the Primate BBB In Vivo

Figure 3:
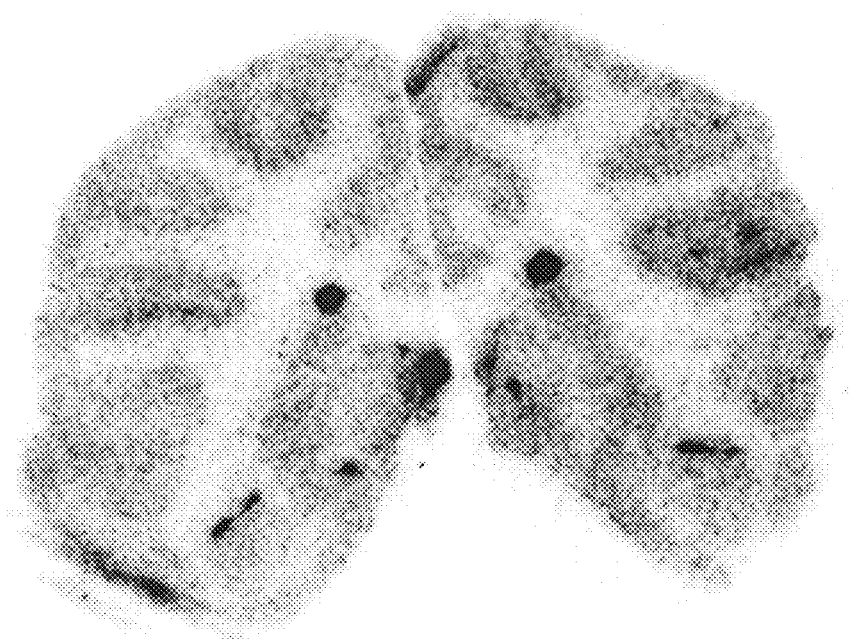
FIG. 3 shows the brain scan of a Rhesus monkey treated with a humanized monoclonal antibody in accordance with the present invention. The [$^{125}$I]-labeled version 5 HIRMAb was injected intravenously in an anesthetized rhesus monkey, and the animal was euthanized 120 minutes later. The brain was rapidly removed and cut into coronal hemispheric slabs, which were immediately frozen. Cryostat sections (20 μm) were cut and exposed to x-ray film. The film was scanned to yield the image shown in FIG. 3. This image shows the clear demarcations between the gray matter and white matter of the primate brain. Owing to the higher vascular density in gray matter, there is a greater uptake of the humanized HIRMAb, relative to white matter.

The humanized Version 5 HIRMAb was radiolabelled with 125-Iodine and injected intravenously into the adult Rhesus monkey. The animal was sacrificed 2 hours later and the brain was removed and frozen. Cryostat sections (20 micron) were cut and applied to X-ray film. Scanning of the film yielded an image of the primate brain uptake of the humanized HIRMAb (FIG. 3). The white matter and gray matter tracts of the primate brain are clearly delineated, with a greater uptake in the gray matter as compared with the white matter. The higher uptake of the human HIRMAb in the gray matter, as compared with the white matter, is consistent with the 3-fold higher vascular density in gray matter, and 3-fold higher nonspecific IgG is injected into Rhesus monkeys there is no brain uptake of the antibody (Pardridge et al., 1995). These film autoradiography studies show that the humanized HIRMAb is able to carry a drug (iodine) across the primate BBB in vivo. Based on the high binding of the humanized HIRMAb to the human BBB (FIG. 2), similar findings of high brain uptake in vivo would be recorded in humans.

EXAMPLE 5

Affinity Maturation of the Antibody by CDR or FR Amino Acid Substitution

The amino acid sequences of the VH of the HC and of the VL of the LC are given in FIG. 4 for the Version 5 humanized HIRMAb, the murine 83-14 HIRMAb, and either the B43 HC or the REI LC antibodies. Given the CDR amino sequences in FIG. 4, those skilled in the art of antibody engineering (Schier et al., 1996) may make certain amino acid substitutions in the 83-14 HC or LC CDR sequences in a process called "affinity maturation" or molecular evolution. This may be performed either randomly or guided by x-ray diffraction models of immunoglobulin structure, similar to single amino acid changes made in the FR regions of either the HC or the LC of an antibody (U.S. Pat. No. 5,585,089). Similarly, given the FR amino acid sequences in FIG. 4, those skilled in the art can make certain amino acid substitutions in the HC or LC FR regions to further optimize the affinity of the HIRMAb for the target HIR antigen. The substitutions should be made keeping in mind the sequence identity limitations set forth previously for both the FR and CDR regions. These changes may lead to either increased binding or increased endocytosis or both.

EXAMPLE 6

Figure 5:
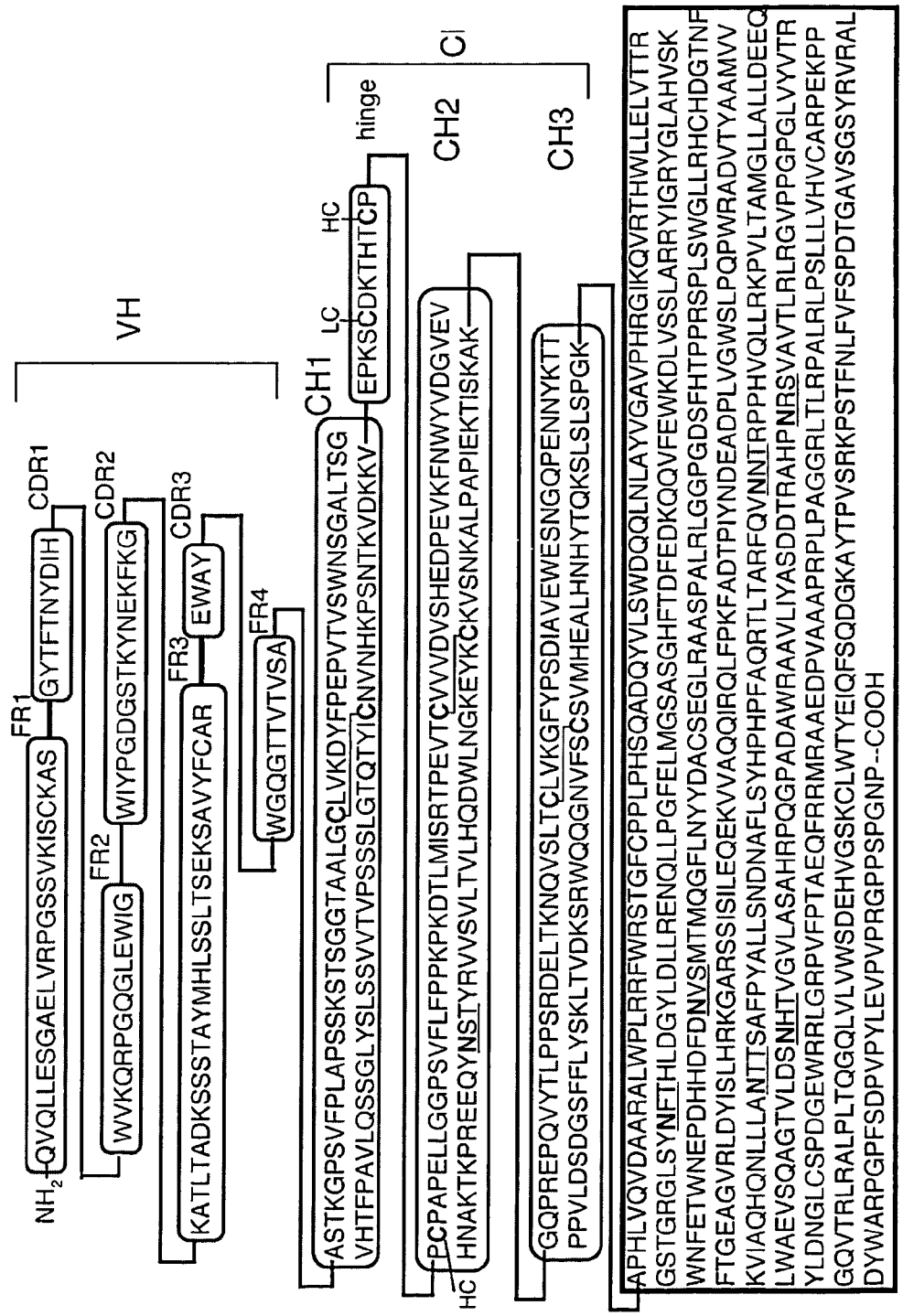
FIG. 5 shows the amino acid sequence of a fusion protein of human α-L-iduronidase (IDUA) (SEQ. ID. NO. 48), which is fused to the carboxyl terminus of the heavy chain (HC) of the humanized monoclonal antibody to the human insulin receptor (HIRMAb). The HC is comprised of a variable region (VH) and a constant region (CH); the CH is further comprised of 3 sub-regions, CH1 (SEQ. ID. NO. 44), CH2 (SEQ. ID. NO. 45), and CH3 (SEQ. ID NO. 46); the CH1 and CH2 regions are connected by a 12 amino acid hinge region (SEQ. ID. NO. 47). The VH is comprised of 4 framework regions (FR1=SEQ. ID. NO. 30; FR2=SEQ. ID. NO. 32; FR3=SEQ. ID. NO. 34; and FR4=SEQ. ID. NO. 36) and 3 complementarity determining regions (CDR) (CDR1=SEQ. ID. NO. 31; CDR2=SEQ. ID. NO. 33; and CDR3=SEQ. ID. NO. 35). The amino acid sequence shown for the CH is well known in existing databases and corresponds to the CH sequence of human IgG1. There is a single N-linked glycosylation site on the asparagine (N) residue within the CH2 region of the CH, and there are 6 potential N-linked glycosylation sites within the IDUA sequence, as indicated by the underline.

Humanized HIRMAb/α-L-iduronidase Fusion Protein

α-L-iduronidase (IDUA) is the enzyme missing in patients with Hurler syndrome or type I mucopolysaccharidosis (MPS), which adversely affects the brain. The brain pathology ultimately results in early death for children carrying this genetic disease. IDUA enzyme replacement therapy (ERT) for patients with MPS type I is not effective for the brain disease, because the enzyme does not cross the BBB. This is a serious problem and means the children with this disease will die early even though they are on ERT. The enzyme could be delivered across the human BBB following peripheral administration providing the enzyme is attached to a molecular Trojan horse such as the humanized HIRMAb. The IDUA may be attached to the humanized HIRMAb with avidin-biotin technology. In this approach, the IDUA enzyme is mono-biotinylated in parallel with the production of a fusion protein of the humanized HIRMAb and avidin. In addition, the IDUA could be attached to the humanized HIRMAb not with avidin-biotin technology, but with genetic engineering that avoids the need for biotinylation or the use of foreign proteins such as avidin. In this approach, the gene encoding for IDUA is fused to the region of the humanized HIRMAb heavy chain or light chain gene corresponding to the amino or carboxyl terminus of the HIRMAb heavy or light chain protein. Following construction of the fusion gene and insertion into an appropriate prokaryotic or eukaryotic expression vector, the HIRMAb/IDUA fusion protein is mass produced for purification and manufacturing. The amino acid sequence and general structure of a typical MAb/IDUA fusion protein is shown in FIG. 5 (SEQ. ID. NO. 48). In this construct, the enzyme is fused to the carboxy terminus of the heavy chain (HC) of the humanized HIRMAb. The amino acid sequence for the IDUA shown in FIG. 5 is that of the mature, processed enzyme. Alternatively, the enzyme could be fused to the amino terminus of the HIRMAb HC or the amino or carboxyl termini of the humanized HIRMAb light chain (LC). In addition, one or more amino acids within the IDUA sequence could be modified with retention of the biological activity of the enzyme. Fusion proteins of lysosomal enzymes and antibodies have been prepared and these fusion proteins retain biological activity (Haisma et al, 1998). The fusion gene encoding the fusion protein can be inserted in one of several commercially available permanent expression vectors, such as pCEP4, and cell lines can be permanently transfected and selected with hygromycin or other selection agents. The conditioned medium may be concentrated for purification of the recombinant humanized HIRMAb/IDUA fusion protein.

EXAMPLE 7

Role of Light Chain (LC) in Binding of HIRMAb to the Human Insulin Receptor

Myeloma cells (NSO) were transfected with a plasmid encoding the either the humanized HIRMAb light chain or "surrogate light chain", which was an anti-dansyl MAb light chain (Shin and Morrison, 1990). The anti-dansyl light chain is derived from the anti-dansyl IgG, where dansyl is a common hapten used in antibody generation. Both the myeloma line transfected with the humanized HIRMAb light chain, and the myeloma line transfected with the surrogate light chain were subsequently transfected with a plasmid encoding the heavy chain of the chimeric HIRMAb. One cell line secreted an IgG comprised of the anti-HIRMAb chimeric heavy chain and the anti-HIRMAb humanized light chain, and this IgG is designated chimeric HIRMAb heavy chain/humanized HIRMAb light chain IgG. The other cell line secreted an IgG comprised of a chimeric HIRMAb heavy chain and the anti-dansyl light chain, and this IgG is designated chimeric HIRMAb HC/dansyl LC IgG. Both cells lines secreted IgG processed with either the humanized HIRMAb light chain or the anti-dansyl light chain, as determined with a human IgG ELISA on the myeloma supernatants. These data indicated the chimeric HIRMAb heavy chain could be processed and secreted by myeloma cells producing a non-specific or surrogate light chain. The reactivity of these chimeric antibodies with the soluble extracellular domain (ECD) of the HIR was determined by ELISA. The HIR ECD was purified by lectin affinity chromatography of the conditioned medium of CHO cells transfected with the HIR ECD as described previously (Coloma et al, 2000). In the HIR ECD ELISA, the murine 83-14 HIRMAb was used as a positive control and mouse IgG2a was used as a negative control. The negative control produced negligible ELISA signals; the standard curve with the murine 83-14 MAb gave a linear increase in absorbance that reached saturation at 1 μg/ml murine 83-14 MAb. The immune reaction in the ELISA was quantified with a spectrophotometer and maximum absorbance at 405 nm (A405) in this assay was 0.9. All isolated myeloma clones secreting the chimeric HIRMAb heavy chain/humanized HIRMAb light chain IgG were positive in the HIR ECD ELISA with immuno-reactive levels that maximized the standard curve. In addition, the myeloma clones secreting the chimeric HIRMAb HC/dansyl LC IgG also produced positive signals in the HIR ECD ELISA, and the A405 levels were approximately 50% of the A405 levels obtained with the chimeric HIRMAb heavy chain/humanized HIRMAb light chain IgG. These findings indicate the light chain plays a minor role in binding of the HIRMAb to its target antigen, which is the extracellular domain of the human insulin receptor. This interpretation is supported by the finding that no FR substitutions in the humanized LC were required to enable active binding of the humanized HIRMAb to the HIR ECD (see Example 2). These findings show that large variations in the amino acid sequence of the HIRMAb light chain (50% and more) can be made with minimal loss of binding of the intact humanized HIRMAb to the target HIR antigen. Accordingly, a wide variety of LC's may be used to prepare humanized antibodies in accordance with the present invention provided that they are compatible with the HC. The LC is considered to be "compatible" with the HC if the LC can be combined with the HC and not destroy the ability of the resulting antibody to bind to the HIR. In addition, the LC must be human or sufficiently humanized so that any immunogenic reaction in humans is minimized. Routine experimentation can be used to determine whether a selected human or humanized LC sequence is compatible with the HC.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the above preferred embodiments and examples, but is only limited by the following claims.

BIBLIOGRAPHY

Bruggemann, M. et al. (1989) "The immunogenicity of chimeric antibodies," *J. Exp. Med.*, 170:2153-2157.

Coloma, M. J., Lee, H. J., Kurihara, A., Landaw, E. M., Boado, R. J., Morrison, S. L., and Pardridge, W. M. (2000) "Transport across the primate blood-brain barrier of a genetically engineered chimeric monoclonal antibody to the human insulin receptor," *Pharm. Res.*, 17:266-274.

Coloma, M. J., Hastings, A., Wims, L. A., and Morrison, S. L. (1992) "Novel vectors for the expression of antibody molecules using variable regions generated by polymerase chain reaction," *J. Immunol. Methods*, 152:89-104.

Foote, J. and Winter, G. (1992) "Antibody framework residues affecting the conformation of the hypervariable loops," *J. Mol. Biol.*, 224:487-499.

Graziano, R. F. et al. (1995) "Construction and characterization of a humanized anti-γ-Ig receptor type I (FcγRI) monoclonal antibody," *J. Immunol.*, 155:4996-5002.

Haisma, J. J. et al (2000) Construction and characterization of a fusion protein of single-chain anti-CD20 antibody and human β-glucuronidase for antibody-directed enzyme pro-drug therapy. *Blood.* 92: 184-190.

Li, J. Y., Sugimura, K., Boado, R. J., Lee, H. J., Zhang, C., Dubel, S., and Pardridge, W. M. (1999) "Genetically engineered brain drug delivery vectors—cloning, expression, and in vivo application of an anti-transferrin receptor single chain antibody-streptavidin fusion gene and protein," *Protein Engineering*, 12:787-796.

Miller, G. (2002) "Breaking down barriers," *Science*, 297: 1116-1118.

Pardridge, W. M. (1997) "Drug delivery to the brain," *J. Cereb. Blood Flow. Metabol.*, 17:713-731.

Pardridge, W. M., Buciak, J. L., and Friden, P. M. (1991) "Selective transport of anti-transferrin receptor antibody through the blood-brain barrier in vivo," *J. Pharmacol. Exp. Ther.*, 259:66-70.

Pardridge, W. M., Kang, Y.-S., Buciak, J. L., and Yang, J. (1995) "Human insulin receptor monoclonal antibody undergoes high affinity binding to human brain capillaries in vitro and rapid transcytosis through the blood-brain barrier in vivo in the primate," *Pharm., Res.* 12:807-816.

Pichla, W. L., Murali, R., and Burnett, R. M. (1997) "The crystal structure of a Fab fragment to the melanoma-associated GD2 ganglioside," *J. Struct. Biol.*, 119:6-16.

Rechavi, G. et al (1983) "Evolutionary aspects of immunoglobulin heavy chain variable region (VH) gene subgroups". *Proc. Natl. Acad. Sci. (U.S.A.)* 80: 855-859.

Schier, R. et al. (1996) "Isolation of picomolar affinity anti-c-erbB-2 single-chain Fv by molecular evolution of the complementarity determining regions in the center of the antibody binding site," *J. Mol. Biol.*, 263:551-557.

Shin, S. U. and Morrison, S. L. (1990) "Expression and characterization of an antibody binding specificity joined to insulin-like growth factor 1: potential applications for cellular targeting". *Proc. Natl. Acad. Sci. U.S.A.* 87: 5322-5326.

Soos, M. A., et al (1986) "Monoclonal antibodies reacting with multiple epitopes on the human insulin receptor". *Biochem. J.* 235: 199-208.

U.S. Pat. No. 5,624,659 (issued Apr. 29, 1997) "Method of Treating Brain Tumors Expressing Tenascin" (Inventors: Darell D. Bigner and Michael R. Zalutsky; Assignee: Duke University).

U.S. Pat. No. 6,287,792 (issued Sep. 11, 2001) "Drug delivery of antisense oligonucleotides and peptides to tissues in vivo and to cells using avidin-biotin technology (Inventors: William M. Pardridge and Ruben J. Boado; Assignee: University of California).

Vogel, C. L. et al. (2002) "Efficacy and safety of trastuzumab as a single agent in first-line treatment of HER2-overexpressing metastatic breast cancer," *J. Clin. Oncol.*, 20:719-726.

Wu, D., Yang, J., and Pardridge, W. M. (1997): "Drug targeting of a peptide radiopharmaceutical through the primate blood-brain barrier in vivo with a monoclonal antibody to the human insulin receptor." *J. Clin. Invest.*, 100: 1804-1812.

Zhang, Y., Lee, H. J., Boado, R. J., and Pardridge, W. M. (2002) "Receptor-mediated delivery of an antisense gene to human brain cancer cells," *J. Gene Med.*, 4:183-194.

What is claimed is:

1. A method for increasing the ability of a neuropharmaceutical agent to cross the human blood brain barrier, the method comprising genetically fusing said neuropharmaceutical agent to a humanized antibody wherein the humanized antibody has antigen specificity for the human insulin receptor; and, wherein the humanized antibody comprises a $V_H$ domain comprising the amino acid sequence of SEQ ID NO: 5, comprises a $V_L$ domain comprising the amino acid sequence of SEQ ID NO: 6, or comprises a $V_H$ domain comprising the amino acid sequence of SEQ ID NO:5 and a $V_L$ domain comprising the amino acid sequence of SEQ ID NO:6.

2. A method according to claim 1, wherein said neuropharmaceutical agent is an enzyme.

3. A method for targeting a pharmaceutical agent to the human insulin receptor in vivo, the method comprising genetically fusing said pharmaceutical agent to a humanized antibody wherein the humanized antibody has antigen specificity for the human insulin receptor; and, wherein the humanized antibody comprises a $V_H$ domain comprising the amino acid sequence of SEQ ID NO: 5, comprises a $V_L$ domain comprising the amino acid sequence of SEQ ID NO: 6, or comprises a $V_H$ domain comprising the amino acid sequence of SEQ ID NO:5 and a $V_L$ domain comprising the amino acid sequence of SEQ ID NO:6.

4. A method according to claim 3, wherein said neuropharmaceutical agent is an enzyme.

5. The method of claim 1, wherein said neuropharmaceutical agent is a human α-iduronidase enzyme (IDUA).

6. The method of claim 3, wherein said neuropharmaceutical agent is a human α-iduronidase enzyme (IDUA).

7. The method of claim 5, wherein the IDUA is fused to the humanized antibody at a carboxyl terminus of a heavy chain of the humanized antibody.

8. The method of claim 6, wherein the IDUA is fused to the humanized antibody at a carboxyl terminus of a heavy chain of the humanized antibody.

* * * * *